(12) United States Patent
Scholten et al.

(10) Patent No.: US 10,548,613 B2
(45) Date of Patent: Feb. 4, 2020

(54) MEDICAL SHAFT-TYPE INSTRUMENT WITH DIFFERENT STORAGE POSITION DISTANCES DUE TO CLAMP ENTRAINING ELEMENTS AND/OR RETAINING LUGS FOR CLAMPS

(71) Applicant: Aesculap AG, Tuttlingen (DE)

(72) Inventors: Thomas Scholten, Tuttlingen (DE); Gunnar Wanke, Kreuzlingen (CH); Jörg Hinrich Timmermann, Wurmlingen (DE); Michael Benk, Wurmlingen (DE); Rainer Wursthorn, VS-Obereschach (DE)

(73) Assignee: Aesculap AG (DE)

( * ) Notice: Subject to any disclaimer, the term of this patent is extended or adjusted under 35 U.S.C. 154(b) by 431 days.

(21) Appl. No.: 15/307,167

(22) PCT Filed: Feb. 5, 2015

(86) PCT No.: PCT/EP2015/052443
§ 371 (c)(1),
(2) Date: Oct. 27, 2016

(87) PCT Pub. No.: WO2015/165602
PCT Pub. Date: Nov. 5, 2015

(65) Prior Publication Data
US 2017/0056019 A1    Mar. 2, 2017

(30) Foreign Application Priority Data

Apr. 28, 2014   (DE) .................... 10 2014 207 900
Apr. 28, 2014   (DE) .................... 10 2014 207 955
Apr. 28, 2014   (DE) .................... 10 2014 207 971

(51) Int. Cl.
*A61B 17/128*   (2006.01)
*A61B 17/122*   (2006.01)
(Continued)

(52) U.S. Cl.
CPC ........ *A61B 17/1285* (2013.01); *A61B 17/122* (2013.01); *A61B 2017/00544* (2013.01);
(Continued)

(58) Field of Classification Search
CPC .............. A61B 17/122; A61B 17/1285; A61B 2017/00544; A61B 2017/2933; A61B 2017/00548; A61B 2017/2937
See application file for complete search history.

(56) References Cited

U.S. PATENT DOCUMENTS

| 4,512,345 A | 4/1985 | Green |
| 5,441,509 A | 8/1995 | Vidal et al. |

(Continued)

FOREIGN PATENT DOCUMENTS

| CN | 101756741 A | 6/2010 |
| DE | 2744816 A1 | 4/1978 |

(Continued)

OTHER PUBLICATIONS

International Search Report and Written Opinion for International Application No. PCT/EP2015/052443, dated Sep. 9, 2015, 23 pages.

(Continued)

*Primary Examiner* — Phong Son H Dang
(74) *Attorney, Agent, or Firm* — RatnerPrestia

(57) ABSTRACT

A medical shaft-type instrument includes an instrument head for applying clamps, the instrument head connectable via an instrument shaft to an instrument handle for actuating the instrument head. The instrument also includes a clip magazine having a housing, in which magazine a plurality of clamps are bunkered at a predetermined storage position spacing to each other according to the storage principle. All of the clamps can be moved forward by one storage position by a reciprocating transport and entraining rail within the (Continued)

Figure 1:
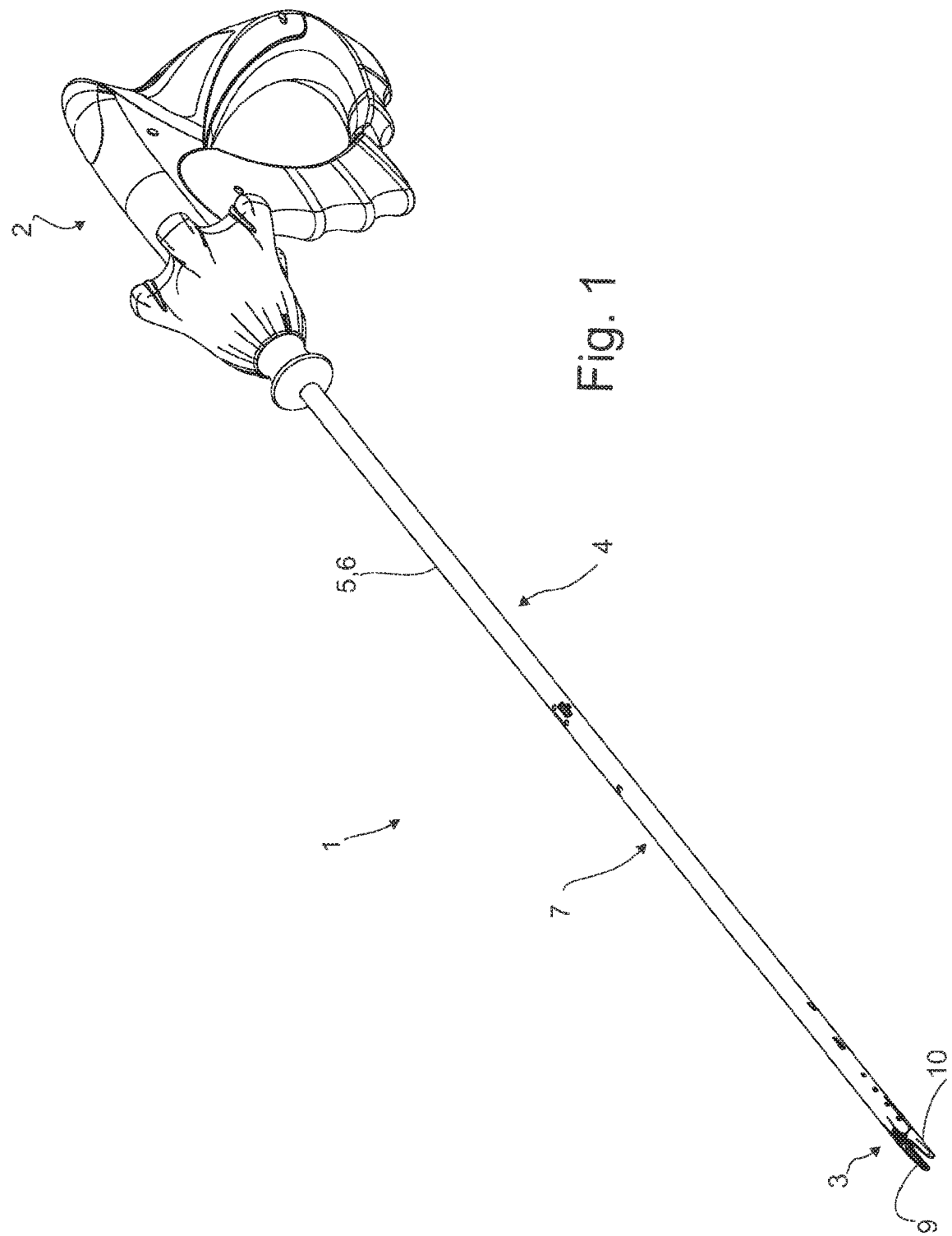

scope of a single delivery stroke. The transport and entraining rail has one clamp entraining element per clamp. The relative distance of the individual clamp entraining elements differs from the respective storage position distances of the clamps in such a way that the entrainment of the bunkered clamps is carried out within the scope of one single delivery stroke in a clocked way.

24 Claims, 19 Drawing Sheets

(51) Int. Cl.
  *A61B 17/00* (2006.01)
  *A61B 17/29* (2006.01)
(52) U.S. Cl.
  CPC ........... *A61B 2017/00548* (2013.01); *A61B 2017/2933* (2013.01); *A61B 2017/2937* (2013.01)

(56) References Cited

U.S. PATENT DOCUMENTS

| | | | | |
|---|---|---|---|---|
| 5,626,585 | A * | 5/1997 | Mittelstadt | A61B 17/1285 227/19 |
| 5,700,271 | A | 12/1997 | Whitfield et al. | |
| 5,833,696 | A | 11/1998 | Whitfield et al. | |
| 6,226,843 | B1 | 5/2001 | Crainich | |
| 7,585,304 | B2 | 9/2009 | Hughett | |
| 7,637,917 | B2 * | 12/2009 | Whitfield | A61B 17/10 606/143 |
| 7,717,926 | B2 | 5/2010 | Whitfield et al. | |
| 7,905,890 | B2 * | 3/2011 | Whitfield | A61B 17/10 606/142 |
| 8,282,655 | B2 | 10/2012 | Whitfield et al. | |
| 8,357,171 | B2 | 1/2013 | Whitfield et al. | |
| 8,382,773 | B2 * | 2/2013 | Whitfield | A61B 17/1285 606/142 |
| 8,409,223 | B2 * | 4/2013 | Sorrentino | A61B 17/10 606/143 |
| 8,579,918 | B2 | 11/2013 | Whitfield et al. | |
| 8,585,718 | B2 * | 11/2013 | Disch | A61B 17/1285 606/143 |
| 8,747,423 | B2 | 6/2014 | Whitfield et al. | |
| 8,814,884 | B2 | 8/2014 | Whitfield et al. | |
| 8,894,666 | B2 * | 11/2014 | Schulz | A61B 17/1285 606/139 |
| 9,011,465 | B2 | 4/2015 | Whitfield et al. | |
| 9,332,989 | B2 | 5/2016 | Morales | |
| 9,364,240 | B2 | 6/2016 | Whitfield et al. | |
| 9,398,917 | B2 * | 7/2016 | Whitfield | A61B 17/1285 |
| 9,439,654 | B2 * | 9/2016 | Sorrentino | A61B 17/1285 |
| 9,498,227 | B2 * | 11/2016 | Zergiebel | A61B 17/128 |
| 9,526,501 | B2 * | 12/2016 | Malkowski | A61B 17/1285 |
| 9,597,089 | B2 | 3/2017 | Menn | |
| 2005/0171560 | A1 | 8/2005 | Hughett | |
| 2006/0079912 | A1 * | 4/2006 | Whitfield | A61B 17/10 606/142 |
| 2006/0079913 | A1 * | 4/2006 | Whitfield | A61B 17/10 606/142 |
| 2006/0085015 | A1 | 4/2006 | Whitfield et al. | |
| 2007/0173866 | A1 | 7/2007 | Sorrentino et al. | |
| 2008/0243145 | A1 * | 10/2008 | Whitfield | A61B 17/1285 606/143 |
| 2008/0312670 | A1 * | 12/2008 | Lutze | A61B 17/122 606/157 |
| 2010/0121351 | A1 | 5/2010 | Whitfield et al. | |
| 2010/0204715 | A1 | 8/2010 | Whitfield et al. | |
| 2010/0222790 | A1 | 9/2010 | Whitfield et al. | |
| 2011/0224701 | A1 | 9/2011 | Menn | |
| 2012/0048759 | A1 * | 3/2012 | Disch | A61B 17/1222 206/339 |
| 2013/0110135 | A1 | 5/2013 | Whitfield et al. | |
| 2013/0150870 | A1 | 6/2013 | Morales | |
| 2013/0190779 | A1 | 7/2013 | Whitfield et al. | |
| 2013/0190780 | A1 | 7/2013 | Whitfield et al. | |
| 2013/0289583 | A1 | 10/2013 | Zergiebel et al. | |
| 2014/0052157 | A1 | 2/2014 | Whitfield et al. | |
| 2014/0330291 | A1 | 11/2014 | Whitfield et al. | |

FOREIGN PATENT DOCUMENTS

| | | |
|---|---|---|
| DE | 69220110 T2 | 10/1997 |
| DE | 69322680 T2 | 6/1999 |
| DE | 202010005263 U1 | 6/2010 |
| DE | 102009018820 A1 | 10/2010 |
| DE | 202010008714 U1 | 12/2010 |
| DE | 102010036713 A1 | 2/2012 |
| DE | 202011109957 U1 | 7/2012 |
| EP | 0086721 A2 | 8/1983 |
| EP | 0089737 A1 | 9/1983 |
| EP | 0409569 A1 | 1/1991 |
| EP | 0697198 A1 | 2/1996 |
| EP | 0769274 A1 | 4/1997 |
| EP | 0503662 A1 | 6/1997 |
| EP | 0834286 A1 | 4/1998 |
| EP | 1712187 A2 | 10/2006 |
| EP | 1810622 B1 | 7/2007 |
| EP | 2158855 A1 | 3/2010 |
| EP | 2609877 A1 | 7/2013 |
| GB | 1592093 | 7/1981 |
| WO | 03005911 A1 | 1/2003 |
| WO | 2007087834 A1 | 8/2007 |
| WO | 2008118928 A2 | 10/2008 |
| WO | 2008127968 A2 | 10/2008 |

OTHER PUBLICATIONS

International Search Report and Written Opinion for International Application No. PCT/EP2015/052445, dated Sep. 9, 2015, 18 pages.
German Search Report for German Application No. 10 2014 207 900.4, dated Mar. 17, 2015 with translation, 15 pages.
German Search Report for German Application No. 10 2014 207 971.3, dated Mar. 13, 2015 with translation, 15 pages.
German Search Report for German Application No. 10 2014 207 955.1, dated Mar. 11, 2015 with translation, 15 pages.
Chinese Office Action for Chinese Application No. 201580025323.9, dated Sep. 29, 2018, with translation, 18 pages.
Non Final Office Action for U.S. Appl. No. 15/307,231, dated Nov. 15, 2018, 19 pages.
Notice of Allowance for U.S. Appl. No. 15/307,231, dated Aug. 5, 2019, 7 pages.
Notice of Allowance for U.S. Appl. No. 15/307,231, dated Oct. 29, 2019, 12 pages.

* cited by examiner

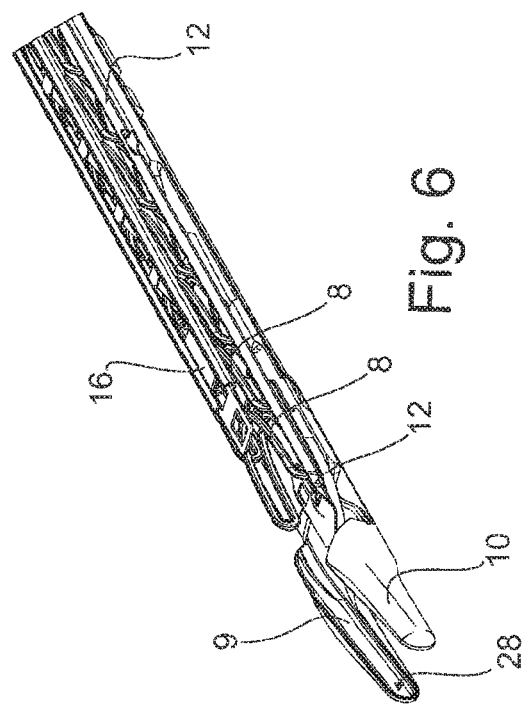

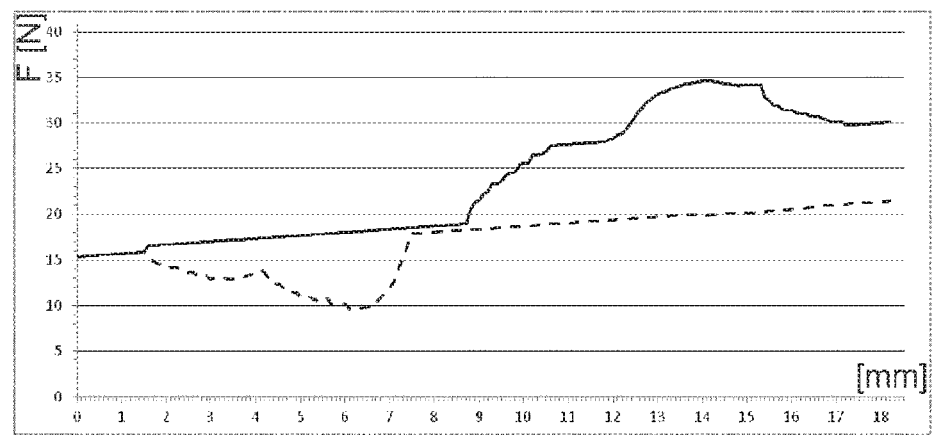
Fig. 9
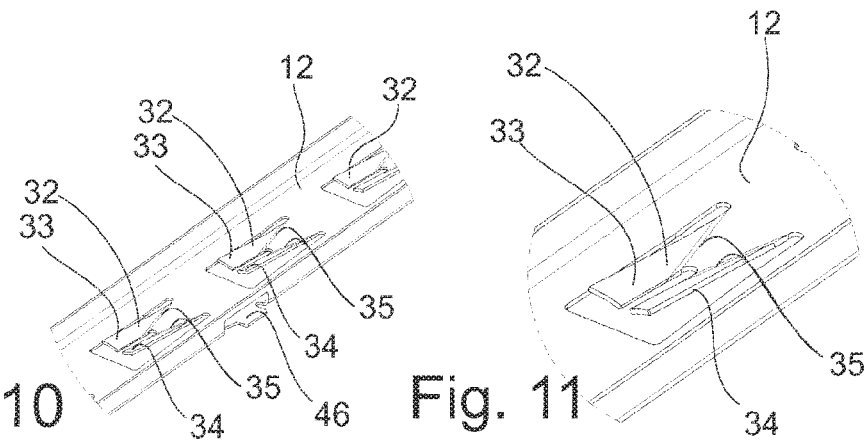
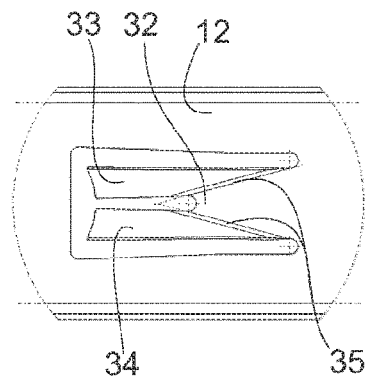
Fig. 12
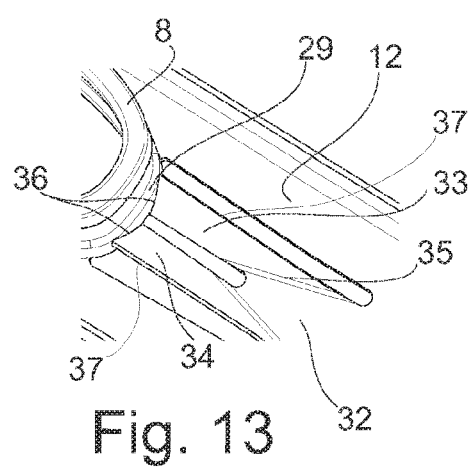
Fig. 13

MEDICAL SHAFT-TYPE INSTRUMENT WITH DIFFERENT STORAGE POSITION DISTANCES DUE TO CLAMP ENTRAINING ELEMENTS AND/OR RETAINING LUGS FOR CLAMPS

RELATED APPLICATION(S)

This application is the United States National Phase entry of International Application No. PCT/EP2015/052443, filed Feb. 5, 2015, which is related to and claims the benefit of priority of German Application No. DE 10 2014 207 900.4, filed Apr. 28, 2014, German Application No. DE 10 2014 207 955.1, filed Apr. 28, 2014, and German Application No. DE 10 2014 207 971.3, filed Apr. 28, 2014, all of the foregoing applications listed in this paragraph being incorporated by reference herein in their entireties.

FIELD

The invention relates to a medical shaft-type instrument, preferably of the minimally invasive type, comprising an instrument head/jaw part for applying clamps such as ligature clamps, clips, or (spring) serrefines, i.e. such components which have a clamping effect after a "plastic/elastic" deformation.

BACKGROUND

Medical shaft-type instruments are already known from prior art, such as from EP 0 697 198 A1. This document discloses a surgical application device for clips. In order to allow a reuse of the essential parts of the application device in a surgical application device provided for U-shaped clips and comprising a handle, a tube shaft connecting thereto, a pincer-shaped contact tool on the free end of the tube shaft and a clip magazine in the tube shaft, comprising a closure mechanism for the contact tool which can be actuated from the handle and is arranged in the tube shaft, and comprising a feed motion mechanism for the clips which can also be actuated from the handle and is arranged in the tube shaft, said document suggests to provide the tube shaft with a lateral opening in which the clip magazine can be detachably inserted from outside in such a manner that it becomes operatively connected with the feed motion mechanism and that the outlet of the clip magazine is aligned with a feed motion path guiding the clips into the contact tool.

Such a clip magazine is also known from DE 10 2009 018 820 A1. In order to the simplify the construction of the magazine and to reduce the size with a magazine comprising a plurality of C-shaped ligature clamps, a housing receiving the ligature clamps which are arranged serially in a row and parallel to one another, a transport element which is able to reciprocate relative to the housing in the direction of the row and causes at least one a ligature clamp to advance toward the outlet end of the magazine upon the forward and backward motion relative to the housing, this document suggests that the ligature clamps each comprise two legs connected via a bridge portion and are subdivided by a longitudinal slit in two portions adjoining each other and connected to each other in the area of the free ends of the leg, and that the transport element penetrates the ligature clamps arranged in a row in the intermediate space between the two adjoining portions of the ligature clamp.

Thus, these existing devices use surgical clamps or clips which are also already known in principle.

By way of example, the company Applied Medical sells a surgical clip named EPIX Universal CA500, in which the two essentially straight clamp webs/legs/clip arms are connected to each other by a substantially V-shaped portion. The two straight clip arms extend substantially parallel to the longitudinal axis of the surgical clip and in the transition zones between the clip arms and the connecting portion, and relative small bending radii are provided in the area of the fillet of the connecting portion. This means that the transition zones are formed by kinks. Comparable surgical clips having a comparable geometry are also marketed by United States Surgical under the name Endo Clip Autosuture 5 mm and by Ethicon under the name Ligamax 5. The Endo Clip Autosuture III 5 mm likewise sold by United States Surgical has a somewhat different geometry. This clip also comprises two substantially straight, parallel clip arms as well as a connecting portion for the two straight clip arms, which is formed with a fillet having a quite small radius of curvature. Other than the surgical clips described above, the transition zones between the clip arms and the connecting portion are formed so as to have a considerably larger radius of curvature, so to speak rather as bent portions than as kinked portions. The Patent application US 2011/0224701 A1 discloses a surgical clip comprising a semicircular outer surface and a profiled inner surface. The semicircular outer surface serves to prevent the clip from getting wedged in the jaw part of a clip applicator and the profiled inner surface serves to improve the adherence on the clamped tissue. As seen in a side view, the clip arms of the clips each comprise straight portions which extend parallel to each other in the area of the distal end of the clip, i.e. at its open side. In addition, the clip arms consist of several substantially non-deformable portions which are connected by deformable portions. All known clips have the common feature that each of the clip arms comprises one substantially straight portion and the connecting portion includes two substantially straight portions. Formed in the fillet as well as in the transition zones between the clip arm and the connecting portion are sections which are curved to a greater or lesser extent. What is more, all these clips are single-web clips, namely clips which can be bent out of a piece of wire and extend substantially in a plane (except for a wire beading).

Single-web clips always have two clip arms. It is a problem with such type of clips that they have unfavorable properties in some cases during applying, i.e. in the course of being compressed by a clip applicator. On the one hand, the provision of the quite small radius of curvature in the transition zone from the clip arm to the connecting portion creates a zone in which the material of the clip (a metal, for instance titanium or titanium alloys) is stretched to a greater extent than in the adjacent zones, having the effect that said zone, in the following referred to as a kinked area, cannot be completely re-deformed into the straight shape when compressing the clip with an applicator. Consequently, the compressed clip will have an area where the two clip arms have a larger distance between them. This results in a suboptimal closure of the clipped, i.e. compressed vessel. A further problem with this kind of clips is that the closure of said clips in the compressed state is weak at the distal end of the clip arms. This means that the distal clip ends hardly apply a force onto the vessel, with said force being supposed to result in the closing of the vessel. During the compression procedure, the two parallel clip arms are deformed inwards around the fillet of the clip. In doing so, only the kinked area or the transition zone of the clip remains in contact with the respective branch of the clip applicator. Only if the distal ends of the clip touch each other (in case no tissue is grasped) or come into contact on both sides of the tissue to be grasped (in case tissue is grasped), the kinked area between the clip arm and the connecting portion is bent up. In this process, the distal ends of the clip arm are deformed towards outside and the relevant point of transmitting the force into the tissue is displaced toward the kinked area. This again releases the distal ends of the clip arms, and they will relax from their elastic deformation (while mostly maintaining their current position). If the kinked area in the clip arm has been re-deformed as far as possible, i.e. the clip is completely pressed, this has the effect that the clip is hardly able to apply a closing or compression force at the distal ends of the clip arms, as the distal ends of the clip arms can be easily deformed outwards in elastic fashion and there are zones in the middle region at which the clip arms contact each other (if no tissue is grasped) or the clip arms have a substantially punctiform contact on both sides of the grasped tissue (in the following, this area is referred to as a middle contact area in both cases). In this way, the distal ends have been fully relieved towards the end of the compression procedure, as the kinked area in the clip arm has been re-deformed with a force which by far exceeds the force which is required for bringing the remaining areas of the clip into the compressed shape of the clip. The compression force, which actually should be distributed over the length of the compressed clip as uniformly as possible, will then be concentrated in the vicinity of the clip fillet and the middle contact area of the clip.

The European Patent application EP 1 712 187 A2 shows an instrument head in which the two jaw part branches are connected via a common base in an elastic/resilient manner. In the area of their distal ends which are provided for holding the surgical clip and compressing it and applying the clip in this way, the two branches have their outer side provided with one sliding surface each. For closing the instrument head and applying the clip, the instrument head is displaced in a proximal end direction with respect to the shaft in which it is arranged (i.e. the instrument head is partially pulled into the shaft or the shaft is slipped over the instrument head), and the distal edge of the shaft glides along the sliding surfaces. Due to the fact that the sliding surfaces are inclined with respect to the axis of the shaft, the distal ends of the branches are urged inwards, whereas the proximal ends of the branches are held by the base. In this way, the branches each perform a rotary movement around that point at which the branches are connected to the base. The opening procedure of the instrument head proceeds without any guidance and is exclusively ensured by the elasticity of the branches which are urged back into their initial position if the instrument head is pushed out of the shaft during the opening procedure.

A comparable instrument head is also shown in the International Patent Application WO 2008/127968, even though the instrument illustrated therein differs greatly from the above-described instrument. The rotary movement of the branches during opening and closing the instrument head is still more apparent from the US Patent application US 2005/0171560 A1. According to this document, the distal areas of two branches are articulated on the base and rotate around the fastening point. Also in this construction, the clip is applied by the distal edge of the shaft gliding along the sliding surfaces which are provided on the outer sides of the branches, and in this way presses the branches in inward direction. The problem with this type of instrument heads is that they always have a closing geometry which is always the same, to be more precise, that first the distal ends of the branches make contact with each other or slide past each other; subsequently, those areas of the branches which are arranged to be further proximal make contact with each other or slide past each other. This means in the case of clip applicators that the clip is always closed starting from the distal end. For other surgical instruments such as endoscopic scissors, this structure of an instrument head is not useful for this reason. A further problem relating to this kind of instrument head is that the process of opening the instrument head is solely achieved by the elasticity of the branches. The opening movement of the instrument head is performed without any guidance. If it should happen that a piece of tissue or some other piece gets between the front edge of the shaft and a branch of the instrument head, the opening procedure of the instrument head could be impeded thereby. In that case, it would be necessary to first remove the instrument from the cavity within the patient, to free it of the piece of tissue, and to insert it into the patient again. This entails delays and disturbances in the surgical procedure.

SUMMARY

The invention relates to a medical shaft-type instrument, preferably of the minimally invasive type, comprising an instrument head/jaw part for applying clamps such as ligature clamps, clips, or (spring) serrefines, i.e. such components which have a clamping effect after a "plastic/elastic" deformation, wherein the instrument head can be connected/is connectable via an instrument shaft to an instrument handle such as a "Challenger Handle" for actuating/operating the instrument head, and comprising a clip magazine having a housing, in which magazine a plurality of clamps are loaded or bunkered at a predetermined storage position spacing relative to each other according to the storage principle/individual storage principle, all the clamps can be moved/are movable forward each by one storage position/rest position/standby position (i.e. that position in which the respective clamp is deposited in the clip magazine when the transport and entraining rail is unmoving) by means of a reciprocatable transport and entraining rail such as in the manner of a feed rail/a metal feed plate within the scope of a single delivery stroke/feed stroke, wherein the transport and entraining rail has (at least) one clamp entraining element.

The instrument head forms a jaw part area by means of an upper and a lower jaw part or an upper and a lower jaw part branch. The instrument handle may be designed as a "Challenger" handle and/or be operated with manual force and/or gas pressure.

The term "clip" is used as a synonym for the term "clamp". A clamp has a non-compressed initial state and a compressed final state. In the compressed state, there is normally some tissue between two matching clamp arms/clip arms, for instance a hollow organ such as a blood vessel. In this case, the thickness and consistency of the wall of the blood vessel dictate the width of the gap between the clamp arms/clip arms in the compressed state.

It is an object of a parallel patent application to provide a surgical clip in which a gap is formed between the clip arms which is uniform and as small as possible and in which the clip arms make available a sufficient compression force towards their distal ends. A further object is to provide a surgical clip which applies a mostly constant force onto the grasped tissue over substantially the entire length of the clip. In this context, another object is to provide a manufacturing method for such a clip.

To this end, the applicant has already developed a solution. In the case of a surgical clip for a surgical clip applicator comprising at least one pair of clip arms, with each of the clip arms comprising a distal end or proximal end and the two clip arms of a pair of clip arms being connected to each other at their proximal ends such so that they define a clip fillet, the above-mentioned object is achieved in said parallel invention in that a tangential angle between a tangent line on a neutral fiber of a clip arm and a perpendicular line on a longitudinal axis of the clip shows an essentially steady increase over the entire length of the clip arm.

The present invention also relates to a medical shaft-type instrument comprising such a surgical clip which may also be referred to as a double-web clip. The clip may be further developed in the manner which has been already described.

It is advantageous for the clip if the tangential angle (at a 6% length on the clip arm) has a value of at most 40°, preferably a value of 30°, and more preferably a value from 20° to 30°. At a length of 15% on the clip arms, the tangential angle may have a value of at least 50°, preferably a value of at least 58° and more preferably a value from 58° to 75°.

It is also advantageous if the tangential angle (at a length of 22% on the clip arm) has a value of at least 60°, preferably a value of at least 67° and more preferably a value from 67° to 80°.

If the tangential angle (at a length of 27% on the clip arm) has a value of at least 65°, preferably a value of at least 72°, and more preferably a value from 72° to 85°, it is possible to achieve an advantageous design of the clip.

At a 100% length on the clip arm, the tangential angle may have a value of at most 88°, preferably a value from 80° to 88°. It is of advantage here if a first derivative of the curvature of a neutral fiber of a clip arm does not have a change of sign in the range of 8% to 100% of the clip arm length; it is more preferable if there is no change of sign over the entire length of the clip arm.

At least two pairs of clip arms may be provided, of which a clip arm of a pair of clip arms may have its distal end connected to at least one distal end of another clip arm of a further pair of clip arms and may define a distal connecting portion. The clip may comprise two or three pairs of clip arms, and it may be formed as an open or closed ring clip or double ring clip, and may be preferably made by stamping, laser sintering, rolling, casting, metal injection molding and/or cutting, in particular laser cutting or water jet cutting.

In the area of the distal end of a clip arm and/or of a distal connecting portion, a recess may be provided which is open toward the proximal end and is closed toward the distal end, so that the recess is accessible from the proximal end and forms a first abutment surface toward the distal end and preferably forms a second abutment surface toward a lateral or medial direction, with the recess being more preferably manufactured by stamping and/or impressing. The recess may be formed in a distal connection area of two distally connected clip arms, preferably by forming the cross-sectional dimensions of the distal connecting portion on the proximal and/or medial side of the clip arm, with a reduction of the cross-sectional dimension being made preferably to distal and/or lateral ends, a tapering being made more preferably to the half cross-sectional dimension.

It is also advantageous if a proximal connection area of two clip arms, a clip arm and/or possibly a distal connecting portion of two clip arms has a variable height and/or width of preferably at least ±10% in at least one direction transverse to the neutral phase. It is expedient if the cross-sectional area of a clip arm and/or of a proximal connection area changes toward the clip fillet, whereby particularly the width of the clip arm and/or of the proximal connection area which is changed, in particular enlarged. Here, at least one clip arm may comprise at least one portion having a wavy shape and/or a zigzag shape in a direction parallel, transverse to and/or perpendicular to the clip's plane. A pair of clip arms may comprise clip arms which change their cross-section laterally, in particular are tapered, preferably by an edge break in the distal region of the clip arm, in particular by an enlarged radius on the outer edge of the clip arm. At least one clip arm may have its inner surface provided with a profile which is preferably formed by means of impressing, rolling, cutting or by electric discharge wire cutting or electric discharge die cutting.

Such surgical clips may be produced in a sequence of steps, for instance by stamping a blank out of sheet metal, wherein the blank remains connected to the remaining sheet metal, at least on one point, preferably in the area of the later clip fillet, a subsequent process of bending the blank in a direction transverse to the remaining sheet metal, so that the clip arms protrude from the sheet metal plane, with the option that said bending process may be carried out in several steps and after which a cutting off from the remaining sheet metal takes place. It is possible to carry out a step of impressing a profile on at least one side of the sheet metal prior to and/or following the process of stamping the blank, wherein the impressing process may be performed in several steps.

The clip arms of a pair of clip arms are usually made in one piece and hence are physically connected to each other. In principle, the clip arms may also be formed to be separate and subsequently be connected to each other by welding, for example.

The object which is achieved in a parallel patent application is to provide an instrument head for a surgical tube shaft instrument with which the closure geometry of the instrument head can be adjusted as needed, on the one hand, and in which the process of closing and opening the jaw part branches is performed in a guided manner, on the other hand.

With a device comprising a jaw part for a surgical tube shaft instrument, comprising a support component, a first branch having a first operating range and a second branch having a second operating range, this object is achieved in that the first branch and/or the second branch comprises one slot-type guide element in each case, and the branches are held in the axial direction by the support component, wherein a cam carrier component/slider is provided which can be shifted relative to the support component in the axial direction and is provided with at least two cams, with each of the slot-type guide elements being adapted to be in contact with at least two cams (and to glide along these) which are provided on the cam carrier component or on the slider, in the event of a relative axial displacement between the support component and the cam carrier component, in order to bring about the opening or closing of the jaw part branches.

The present invention also relates to a medical shaft-type instrument comprising such an instrument head.

Here, it is advantageous if the instrument head is further developed in that the support component is integrally formed with a shaft component of the shaft or is fastened to it and that the cam carrier component is a slider which can be axially moved relative to the shaft. The one jaw part branch/the first branch and the other jaw part branch/the second branch are preferably elastically coupled. Advantageously, at least two slot-type guideways may be formed on at least one slot-type guide element. The first branch and/or the second branch comprise(s) e.g. a protrusion which engages an area of the support component and in this way limits an axial movement of the branch with respect to the support component and preferably prevents said movement.

The at least one protrusion may be provided on a flexible extension of the related slot-type guide elements of the branch and the resilient extension may be able to urge the protrusion toward the support component and in this way ensure the engagement of the at least one protrusion in the support component, with the elasticity of bending of the extension being adjusted such that the movability and the movements of the slot-type guide element and the operating range are essentially not impaired by the extension. At least one slot-type guide element may be designed so as to have an essentially sheet-like design; the cam carrier component may be designed so as to have an essentially sheet-like design, and the at least one slot-type guide element may only rest against a flat side of the cam carrier component which is designed as a sandwich-like structure; preferably, one slot-type guide element each is arranged on two sides of the cam carrier component.

The cam carrier component and at least one slot-type guide element may define at least one area in which a slot-type guideway and the pertaining cam of the cam carrier component form an undercut, so that the slot-type guide element lifting off from the cam carrier component is prevented; it is preferred here that at least one area of an undercut is present across the entire range of motion of the slot-type guide element to the cam carrier component from a completely opened position to a completely closed position of the instrument head. Further, the surgical instrument may be a surgical clip applicator and the branches of the instrument head may be adapted to support a surgical clip and to apply it by closing the instrument head, wherein the surgical clip preferably is a double-web more preferably consisting of two clip halves which are each (firmly) connected to each other at their two distal ends. The operating ranges of the two branches of the instrument head may be adapted to be shifted—by a clip which is arranged in the instrument head—towards outside and beyond the lateral position of the operating range of the branches in the completely opened position of the instrument head, which can be achieved by the operating ranges in the completely opened position of the instrument head if there is no clip in the instrument head. At least three slot-type guideways may be provided on at least one slot-type guide element, and at any point in time during the opening and closing procedure of the instrument head, at least two slot-type guideways rest against respective cams which are provided on the cam carrier.

The instrument head may comprise a clip storage means/a clip magazine which can be attached in a preferably exchangeable manner, in that a plurality of clips/clamps is provided, wherein the clip storage means/the clip magazine is at least partially arranged in a plane which is parallel to a sandwich-like structure of the at least one slot-type guide element including the cam carrier component, wherein the clips can be supplied at least partially in a clip storage means passing a sandwich-like stacked structure toward the distal areas of the branches. In a special embodiment, at least the operating ranges of the first branch and second branch comprise a movement curve which is symmetrical with respect to a central axis of the instrument head. The surgical instrument may be designed as a pair of scissors, a needle holder, a serrefine or similar surgical instrument, in which the two branches can be moved towards each other and/or past each other. It is to be noted that the symmetrical movement curve does not necessarily have to be symmetrical, but may be adjustable. Indeed, it is even possible that one branch moves toward the line of symmetry and the other moves away from it, but at a lower speed.

The instrument head may also be provided for a surgical tube shaft instrument comprising a first branch having a first operating range and a second branch having a second operating range and may be further developed such that the first branch and/or the second branch comprise(s) one slot-type guide element in each case and the branches are retained in the axial direction, and a cam carrier component is provided which can be shifted in the axial direction relative to the at least one slot-type guide element, wherein the at least one slot-type guide element and the cam carrier component are realized in a substantially flat design and are arranged one above the other in a substantially layered fashion. The cam carrier component and at least one slot-type guide element may comprise at least one area in which they form an undercut, so that the slot-type guide element is prevented from lifting off from the cam carrier component, while it is preferred here that at least one area of an undercut is present over the entire range of motion of the slot-type guide element toward the cam carrier component from a completely opened position into a completely closed position of the jaw part.

The cam carrier component may be provided with at least one cam which rests against a slot-type guideway at least for a partial axial translation of the cam carrier component relative to the slot-type guide element, which guideway is formed on the slot-type guide element wherein the cam—on the side of its axial cross-section facing the slot-type guideway—is substantially realized with a Z-shape, an S-shape or a combination therefrom. It should be mentioned that the cam carrier component may be provided with at least one cam which rests against a slot-type guideway at least for a part of the axial translation of the cam carrier component relative to the slot-type guide element, which guideway is formed on the slot-type guide element wherein the cam—on the side of its axial cross-section facing the slot-type guideway—is substantially realized with a Z-shape, an S-shape or a combination therefrom. Even the cam and the slot-type guideway basically may have an S-shape at the respectively facing sides of its cross-section, and the cam and the slot-type guideway may form in this way a sort of bulge and a fillet, with said bulge of a component protruding into the fillet of the other component, respectively.

A straight portion may be formed between the bulge and the fillet of the cam and/or of the slot-type guideway, wherein this straight portion is inclined preferably with respect to the opening or closing direction of the instrument head, more preferably by more than 7°, in particular less than 20°. The curvature of the bulge of the slot-type guideway may be smaller than the curvature of the fillet of the slot-type guideway and/or the curvature of the bulge of the cam may be larger than the curvature of the fillet of the cam. The curvature of the bulge of the slot-type guideway may be larger than the curvature of the fillet of the cam and/or the curvature of the bulge of the cam may be larger than the curvature of the fillet of the slot-type guideway. The direction of the transmission of force from the cam into the slot-type guideway may be inclined with respect to the opening or closing direction of the instrument head, preferably in a range of up to 20°. Further, the surface area of the cam may face the central axis of the cam carrier component in the area of the point of contact with the slot-type guideway. The device is further developed in an advantageous way if the at least one slot-type guide element extends substantially over the entire width of the cam carrier component, so that the respective cam of the cam carrier component is largely covered by the corresponding slot-type guide element.

At least one slot-type guide element may comprise at least two slot-type guideways each forming an undercut with a corresponding number of cams on the cam carrier ring over a part of the axial displacement of the two components relative to each other from a completely opened position to a completely closed position of the instrument head, wherein the undercuts allow for the assembly of a cam carrier component and a slot-type guide element exclusively in that they can be screwed into each other or are screwed into each other.

If the slot-type guide element and the cam carrier component are in a mounted position after the screwing and assembly process, which is outside the relative axial translation of the slot-type guide element and the cam carrier component from a completely opened position to a completely closed position of the component, a further optimized embodiment can be achieved. The first branch and the second branch each may have a slot-type guide element and the branches may be retained in the axial direction, and a cam carrier component may be provided which is movable in the axial direction relative to the at least one slot-type guide element, wherein the slot-type guide elements are realized in a substantially flat design and are arranged one above the other in a substantially layered manner, the cam carrier component having a substantially hollow cross-section in which the slot-type guide elements are arranged. In a mounted position, the slot-type guide component and the cam carrier component are moved or can be moved into a completely opened position by an axial displacement relative to each other.

In this context, it is advantageous to implement a method of assembling a branch and a cam carrier component for an instrument head which uses the following steps: providing a branch and a cam carrier component in a state in which a slot-type guide element of the branch faces the associated side of the cam carrier component, wherein the branch and the cam carrier component are arranged in two parallel planes spaced from each other, and the longitudinal axes of the two components form a specific angle between them, approaching the branch and the cam carrier component until they make contact with each other, and rotating the branch and the cam carrier component relative to each other in the plane determined by their contact area in such a manner that the angle between their longitudinal axes is reduced, until at least one cam of the cam carrier component on both sides of the crossing point of the two longitudinal axes achieves contact with a slot-type guideway.

A shaft component and a fastening rod may be added by the following steps: providing a branch and a cam carrier component in a state in which a slot-type guide element of the branch faces the associated side of the cam carrier component, wherein the branch and the cam carrier component are arranged in two parallel planes spaced from each other, and the longitudinal axes of the two components form a specific angle between them, approaching the branch and the cam carrier component until they make contact with each other, and rotating the branch and the cam carrier component relative to each other in the plane determined by their contact area in such a manner that the angle between their longitudinal axes is reduced, until at least one cam of the cam carrier component on both sides of the crossing point of the two longitudinal axes achieves contact with a slot-type guideway of the branch, attaching another branch to the opposite side of the cam carrier component, with the option that this step may also be carried out at the outset of the method, and inserting the proximal end of the instrument head into a distal end of the shaft component, wherein the branch and/or the other branch as well as the cam carrier component engage the shaft component or the actuation rod at different points in time, resulting in an axial displacement between the cam carrier component and the branch and/or the other branch into a position which corresponds to the completely opened position of the instrument head.

However, the medical shaft-type instruments of the type initially mentioned are still to be optimized with respect to the guidance of the clamps or clips. The clamps should be able to be conveyed in a precise manner and any jamming situation should be avoided.

It is the object of the present invention to provide a manipulation of the clamps which is as smooth as possible; in particular, the moving of the clamps should take place with low friction and/or low jerking, and abrupt changes in force should be avoided. The aim is to realize a jerk-free transport.

This object is achieved according to the invention in that the relative distance of the individual clamp entraining elements, as seen in the axial direction, differs from the respective storage position distances of the clamps such that the entrainment of the loaded clamps occurs in a clocked way/in staggered intervals within the scope a single delivery stroke. In this case, the force curve in the device will show a favorable course in operation, and impacts and jerks will be avoided.

In this context, it is also advantageous in terms of the force progression if the means transporting and guiding the clamps, such as the transport and entraining rail as well as a retaining rail/a metal retaining plate, and the clamps are adapted to one another such that the clamps are deposited in the shaft-type instrument with different distances between two delivery strokes, in fact with distances different from those defined by the transporting means (alone), such as the clamp entraining elements or similar advancing elements.

It is also advantageous in terms of precision if the clamp entraining elements, the storage positions predetermined by retaining lugs of a retaining rail/support rail, the clamps themselves as well as the transport and entraining rail moving the clamps during its movement in the distal direction are adapted to one another such that first a proximal clamp and subsequently, during the delivery stroke, the distally downstream clamps (one by one) are moved or first a distal clamp and subsequently the proximally upstream clamps are moved (one by one).

The distances between the clamp entrainment elements may be different (as seen in the axial direction); by way of example, they may either increase uniformly or abruptly or decrease uniformly or abruptly toward a distal end of the instrument head.

If the distances between the retaining lugs (as seen in the axial direction) differ from each other and preferably either increase uniformly or abruptly or decrease uniformly or abruptly toward a distal end of the instrument head, another advantageous embodiment may be achieved.

It is expedient here if the distances between the individual clamp entraining elements (exactly) correspond to the distances between the individual retaining lugs or if the relative change in the distances between the clamp entraining elements on the one hand and the retaining lugs on the other hand is smaller or larger.

An advantageous exemplary embodiment is also characterized in that the retaining lug/lugs, when run over by the clamps during their way to the distal end of the instrument head, is/are bound on the retaining rail in a bendable or swiveling way out of the motion path of the clamps to a sufficient extent, wherein during the retraction of the advancing element the transport elements get out of the way.

For avoiding the occurrence of too many frictional forces, it is advantageous if the retaining lug/lugs, in the manner of a butterfly lug, is/are bound in a bendable or swiveling way about a bending or swivel axis which is aligned transverse to the longitudinal direction of the retaining rail, preferably as integral constituent parts of the retaining rail. The concept regarding the bending property and/or pivoting property, as realized with the retaining lugs, can also be transferred to the clamp entraining elements.

It is also advantageous if two wings of a butterfly lug form a retaining lug, with each of the wings being bendable or swiveling about a bending or swivel axis crossing one another distally or proximally relative to the retaining lug. This allows for inducing a particularly clever swerving behavior of the retaining lugs.

If the geometry and the material of the retaining lugs are configured such that they lie down (approximately/substantially) flat when run over by the clamps, i.e. extend so as to be oriented in the axial direction, and preferably do not project through the retaining rail away from the clamps, the shaft-type instrument has a particularly slim design. It is possible to integrate additional functions, if the height of at least some of the retaining lugs measured transverse to the axial direction is so large that it guides a one tongue/feed tongue which is guided through the clamps for ejecting the most distal clamp and/or that it prevents or suppresses a buckling of the tongue.

It has proven to be particularly useful if the distances decrease or increase between two clamp entraining elements or two retaining lugs in the distal and/or proximal direction. It is especially advantageous if the average spacing alteration of the form-fitting elements contacting the clamps in relation to the average spacing amounts to approximately 0.1% to 4%, preferably 0.8% to 1.5%, the form-fitting elements representing a part of the transport and entraining rail or of the retaining rail.

In case the retaining rail is made from a metallic material as a (metal) retaining plate, a particularly good stability is achieved. It goes without saying that plastics may be used as well.

In this context, the invention may also be further developed in another way. Thus, the invention also relates to a medical shaft-type instrument, preferably realized with a minimally invasive design, comprising an instrument head for applying clamps, clips or (spring) serrefines, the instrument head being able to be connected/is connectable via an instrument shaft to an instrument handle for actuating the instrument head, and comprising a clip magazine in which a retaining rail/support rail for storing/depositing a number of clamps at a predetermined storage position spacing relative to each other according to the storage principle is fixed, wherein all the clamps are stored such that they can be moved/are movable forward/are moved forward each by (exactly) one storage position by means of a reciprocatable transport and entraining rail within the scope of a single delivery stroke, and the clamp which is closest to the instrument head can be transported/is transported by means of a tongue/feed tongue into the instrument head for being ejected and bent. This further development is characterized in that the retaining rail, the transport and entraining rail and the tongue are arranged in a stacked construction (relative to each other/on top of each other) in particular in the area of the clip magazine.

In terms of a compact design, it is advantageous if the retaining rail, the transport and entraining rail as well as the tongue are arranged stacked upon each other in a direction which is transverse/orthogonal to the direction defined by the longitudinal axis of the shaft-type instrument and extend substantially in the direction of the longitudinal axis defining the axial direction.

Here, it is advantageous for a proper operation if the tongue is arranged between the retaining rail and the transport and entraining rail.

An efficient medical use on site during a ligature is made possible if a jaw part is formed at the distal end of the instrument head, into which distal end the distal clamp can be transferred or is transferred by the tongue for interaction with an element to be treated such as a vessel or an organ.

The invention may also be further developed. Thus, the invention also relates to a medical shaft-type instrument, preferably realized with a minimally invasive design, comprising an instrument head having a jaw part and intended for applying clamps, clips, or spring serrefines, the instrument head being connected via an instrument shaft comprising an outer tube to an instrument handle (inter alia) for operating/actuating the jaw part, and comprising a clip magazine in which a retaining rail/support rail for storing a number/plurality of clamps at a predetermined storage position spacing relative to each other according to the storage principle/individual storage principle is fixed, wherein all the clamps can be moved/are moveable forward each by (exactly) one storage position (toward the distal end) by means of a reciprocatable transport and entraining rail within the scope of a single delivery stroke, and the clamp which is closest to the instrument head can be transported/is transportable by means of a tongue/feed tongue into the jaw part. The further development is characterized in that the transport and entraining rail is bound on the tongue via a coupling device in such a manner that the transport and entraining rail is entrained in the event of a triggered feed motion for a delivery stroke of the tongue upon reaching or exceeding a specific feed travel.

The manufacture can be simplified if the coupling device is formed in the manner of a feed divider as a component which is separate from the tongue and the transport and entraining rail or is formed as a component (integral and/or made of one material) which is realized in one piece with the tongue or the transport and entraining rail.

Further, it is advantageous if the coupling device uses a cam/elongated hole combination for a delayed transmission of forces and movements from a feed rod to the transport and entraining rail, the tongue being directly/firmly connected to a drive train.

It is expedient if a tongue-side cam engages an elongated hole on the transport and entraining rail side for establishing a form lock.

The invention is also subject-matter of a further development. It also relates to a medical shaft-type instrument, preferably realized with a minimally invasive design, comprising an instrument head having at least one jaw part and intended for applying clamps, clips or (spring) serrefines, which instrument head is able to be connected/connectable, via an instrument shaft comprising an outer tube, to an instrument handle for operating/actuating the instrument head, and comprising a clip magazine in which a retaining rail/support rail for storing clamps at a predetermined storage position spacing relative to each other according to the storage principle/individual storage principle is fixed, wherein all the clamps can be moved/are movable forward by (exactly) one storage position by means of a reciprocatable transport and entraining rail within the scope of a single delivery stroke, for which purpose retaining lugs spaced from each other, on the one hand, and clamp entraining elements on the other hand are provided on the retaining rail and on the transport and entraining rail, said retaining lugs and clamp entraining elements, when the clamps slide over them, being designed so as to swivel away out of the clamp slipway in the respectively other direction in an elastic fashion. This further development is characterized in that all or a number of the retaining lugs and/or clamp entraining elements are realized in a butterfly shape, which is formed with two stop wings tilted relative to each other in the transport direction/delivery stroke direction, and/or a number of the retaining lugs and/or clamp entraining elements is formed so as to have a supporting wedge shape, comprising a tip which is pivotable transverse to the transport direction and is provided at their distal free edge.

In this arrangement, a stop plate or stop face is formed on the retaining lugs and/or on the clamp entraining elements preferably so as to extend substantially perpendicular or at least oblique to the transport direction, for instance in the area of the tip.

It is expedient if the tongue is supported by the transport and entraining rail and/or the retaining rail.

It is also advantageous if spring lugs project from the retaining rail toward the tongue in a supportive manner, preferably two adjacent spring lugs in the area of the distal end of the tongue. Primarily, both spring lugs point toward the proximal end or one of them points toward the proximal end, while the other points toward the distal end.

The invention also relates to a further development, namely a medical shaft-type instrument, which may also be referred to as a tube shaft instrument, preferably realized with a minimally invasive design, comprising an instrument head for applying clamps such as ligature clamps, clips or serrefines, wherein these components to be applied are prepared for being plastically deformed, the instrument head further being connectable, via an instrument shaft comprising an outer tube/sheathing tube, to an instrument handle for operating/actuating the instrument head, and comprising a clip magazine having a housing, in which magazine a number/a plurality of clamps are loaded/stored or are able to be loaded/stored according to the storage principle/individual storage principle.

The further development consists of the clip magazine being integrated in the instrument shaft by the housing of the clip magazine being formed by the outer tube of the instrument shaft itself. On said outer tube, the clamps are slidably supported at least in part or can be slidably supported at least in part.

This further development may be skillfully improved by supplements.

Thus, it is advantageous if the outer tube is provided with at least two contact surfaces/abutment surfaces which are spaced in circumferential direction and permit contact by one or more clamps in a sliding fashion. Over the entire length during a guide stroke or only a partial length thereof, a sliding surface having a relative low friction coefficient can be provided for the clamps on one of their outer sides.

In this context, it is advantageous if two, three or four contact surfaces spaced in circumferential direction are formed, for instance, with one of the clamps or all the clamps. A high tilt protection is achieved by the plurality of contact surfaces.

Furthermore, it is expedient if two contact surfaces are provided for contacting a leg of the clamp, preferably at different points. This means that the outer tube is especially and explicitly prepared for making a direct contact with clamp portions to allow a forward sliding motion in a precise manner. If, on the one hand, the contact surfaces are formed on the inner side of the outer tube or, on the other hand, are formed on slots and/or grooves in the outer tube which are aligned in longitudinal direction and provided on the inner side of the tube, a projection or penetration by clamps can be prevented, on the one hand, and it is possible to realize the outer tube with a smaller diameter, on the other hand, so that a particularly compact construction is achieved.

An advantageous embodiment may be implemented in said second case in that the slots extend completely through the wall of the outer tube or in that grooves, for instance at the radially outer side, are closed on one side. On the one hand, the contact surfaces may be formed only by embossing portions, beads, flanges, slots or grooves; on the other hand, the slits and grooves form the contact surfaces. In this way, some legs of the clamp/clip may protrude through the outer tube while other legs may be slidably arranged exclusively within the outer tube, allowing a use of the instrument as needed.

If the outer tube is formed as a stiffening sheet metal tube, for instance is made of stainless steel, or as a plastic tube/glass tube/ceramic tube (round or cornered cross-section), it is possible to apply materials which are predestinated for medical use.

The outer tube may have an annular cross-section, a cornered cross-section or an oval cross-section. This allows an easier and versatile design of adequate configurations of a medical shaft-type instrument which are optimized for the respective use.

Thus, it is advantageous if the inner diameter of the outer tube and/or the position of the contact surfaces are matched with the clamps to be applied such that the clamp(s), when used or in the interior of the instrument prior to leaving the instrument, are in a preloaded state or are preloaded at least for a short time.

It is advantageous if one clamp or more clamps is/are inserted such that two of its/their clamp webs/webs rest against the contact surfaces. The clamp may be configured as a double-web clip or alternatively as a single-web clip.

The invention also relates to a further development, namely a medical shaft-type instrument preferably of the minimally invasive type, comprising an instrument head having at least one jaw part and intended for applying clamps, clips or (spring) serrefines, i.e. plastically deformable constricting elements, by means of two jaw part branches which can be moved in a scissor-like fashion, wherein the instrument head, via an instrument shaft comprising an outer tube, is able to be connected to an instrument handle (inter alia) for operating/actuating the jaw part, and comprising a clip magazine in which a retaining rail/support rail for storing a number of clamps at a predetermined storage position spacing relative to each other according to the storage principle/individual storage principle is fixed, wherein all the clamps can be moved forward by one storage position by means of a reciprocating transport and entraining rail (such as in the manner of a metal feed plate) within the scope of a single delivery stroke toward the distal end of the instrument shaft, and the clamp which is closest to the instrument head can be transported by means of a tongue/feed tongue into the jaw part between the jaw part branches. The further development is characterized in that the retaining rail comprises an abutment plate or bridge extending in the distal direction, for instance in the manner of a plate-shaped or web-shaped prolonged portion, covering a jaw part area in the region of the one jaw part branch on the side facing the other jaw part branch such that a clamp which has been moved forward or can be moved forward is prevented from tilting toward the one jaw part branch.

A vessel may simply be compressed if the one jaw part branch—due to gravity—is a lower jaw part branch.

A safe application process is possible if one of the jaw part branches or both jaw part branches is/are prepared for a preferably form-fitting reception of a portion of the clamp.

The clamp is held during bending in a particularly safe manner if one of the jaw part branches or each of the jaw part branches is/are shaped as a shell which is open toward the other jaw part branch.

For the purpose of safely guiding the clamp, it is also advantageous if the abutment plate or the bridge, as a guiding or pilot member, protrudes laterally as seen in the longitudinal direction of the retaining rail, for instance on one side.

The invention also relates to a further development, namely a medical shaft-type instrument preferably of the minimally invasive type, comprising an instrument head having at least one jaw part and intended for applying clamps, clips or (spring) serrefines by means of two jaw part branches which can be moved in a scissor-like fashion, wherein the instrument head, via an instrument shaft comprising an outer tube, can be connected to an instrument handle (inter alia) for operating/actuating the jaw part, and comprising a clip magazine in which a retaining rail/support rail for storing a number of clamps at a predetermined storage position spacing relative to each other according to the storage principle/individual storage principle is fixed, wherein all the clamps can be moved forward by one storage position toward the distal end of the instrument shaft by means of a reciprocating transport and entraining rail (such as in the manner of metal feed plate) within the scope of a single delivery stroke, and the clamp which is closest to the instrument head can be transported by means of a tongue/feed tongue into the jaw part between the jaw part branches. The further development is characterized in that the retaining rail has its distal end region provided with a kicker-like or ski jump-like deflector for giving the clamp a final acceleration and/or for deflecting the clamp during its exit from the retaining rail and entering an intermediate space between the two jaw part branches.

It is advantageous if the deflector extends in a manner similar to a ridge in the direction of the tongue and/or of the transport and entraining rail.

It is also expedient if the deflector is formed in a chipless manner as a (guiding) bead.

An advantageous exemplary embodiment is also characterized in that the deflector is provided with an arrow desin/a directional design pointing in the proximal direction.

It is also possible to provide a mounting hole between the deflector and the abutment plate/bridge for the engagement of an assembly tool. Such an assembly tool prepared for being hooked in place extends through the instrument shaft, in particular through the outer tube, facilitating the assembly process.

For the assembly process, it is also advantageous if the mounting hole is formed as a through-hole having a round, oval or cornered outline/cross-section.

In case the deflector, the abutment plate or bridge and the clamp(s) are adapted to one another such that a proximal clamp portion—when run over by the deflector—is lifted up by force and distal clamp web tips are lowered by force, in order to favor a smooth sliding into the jaw part and preferably into the respective jaw part branch, a jerk-free working with the medical shaft-type instrument is facilitated.

The invention can also be developed further, namely as a medical shaft-type instrument preferably of the minimally invasive type, comprising an instrument head having at least one jaw part and intended for applying clamps, clips or (spring) serrefines, which are able to have a constricting effect on organs and vessels by plastic deformation, wherein the instrument head, via an instrument shaft comprising an outer tube, is able to be connected to an instrument handle (inter alia) for operating the jaw part, and comprising a clip magazine in which a retaining rail/support rail for storing a number of clamps at a predetermined storage position spacing relative to each other according to the storage principle/individual storage principle is fixed, wherein all the clamps can be moved forward by one storage position by means of a reciprocating transport and entraining rail within the scope of a single delivery stroke, and the clamp which is closest to the instrument head can be transported by means of a tongue/feed tongue into the jaw part. This further development is characterized in that the tongue is manufactured as a stamped/bent part of a sheet metal material, with the tongue having a distal end plate provided with an insertion recess allowing a portion of the clamp to penetrate/enter into/through the tongue. This allows for a thinner structure of the medical shaft-type instrument and achieves a uniform ejection of the clamp.

It is advantageous if the insertion recess is formed as a through-hole, blind hole, slot, groove or notch.

The insertion recess may have a circular, oval, rectangular, square or polygonal outline or cross-section.

In any case, it is advantageous if the end plate comprises lateral pushing edges or thrust lugs and predefines an open box section together with these.

It is expedient if the open box section is based on a manufacture which involves a bending-, embossing- and/or a flanging step, so that the pushing edges or thrust lugs are formed from crimped sheet metal.

An advantageous exemplary embodiment is also characterized in that the box section is matched with at least the proximal end of the clamp such that the clamp, when entering the jaw part during moving away from the most distal storage position, is guided for the maximum possible length.

If an abutment plate/bridge for the clamp is present in a transition zone between the tongue and a jaw part, which ensures a sliding process free of blocking of the clamp over the transition zone, it is possible to work intraoperatively with relatively low forces.

It is advantageous if the tongue comprises a central tissue spacer pointing toward the distal end.

If the tissue spacer extends towards the distal end beyond the distal extension of the pushing edges or thrust lugs, a further advantageous embodiment can be realized.

The invention is also subject-matter of another further development, also relating to a medical shaft-type instrument preferably of the minimally invasive type, comprising an instrument head (having at least one jaw part) intended for applying clamps, clips or (spring) serrefines, wherein the instrument head, via an instrument shaft comprising an outer tube, can be connected to an instrument handle (inter alia) for actuating at least one jaw part, and comprising a clip magazine in which a retaining rail/support rail for storing a number of clamps at a predetermined storage position spacing relative to each other according to the storage principle/individual storage principle is fixed, wherein all the clamps can be moved forward by one storage position by means of a reciprocating transport and entraining rail within the scope of a single delivery stroke, and the clamp which is closest to the instrument head can be transported by means of a tongue/feed tongue into the jaw part. The further development is characterized in that the tongue as a stamped/bent part is manufactured from a sheet metal material, wherein two web-like pushing edges or thrust lugs are provided on one side of the tongue in the distal end region.

For a trouble-free operation, it is advantageous here if the pushing edges or thrust lugs are matched with the shape of the clamp.

It is expedient here if the pushing edges or thrust lugs at the margin of the tongue, extending in longitudinal direction, flank the insertion recess. This results in a better protection against buckling.

In the end, a double-web clip applicator is made available. It goes without saying that said clip applicator is also capable of applying single-web clips. The functioning of such a medical shaft-type instrument is briefly explained in the following.

If the handle is operated like a "Challenger Handle", an outer lobe of the handle is axially moved toward the distal end and acts on a directly adjacent pusher tube with a stroke and a force oriented in the axis of the shaft. A spring stop firmly connected to the pusher tube is pushed against a return spring which is supported on the shaft tube, whereby the spring force increases. The pusher tube directs the movement directly to a slider of a jaw part packet, which is firmly connected to the pusher tube by means of a bracket, and causes it to move. The jaw part packet may also be referred to as an instrument head. The slider located between two jaw part shafts, which may also be referred to as jaw part branches, converts the axial movement into a closing movement of the jaw parts. The cams of the slider rest against the slot-type guideway of the jaw parts and urge the latter inwards, whereupon the jaw parts move toward each other and compress the clip or clamp present therebetween.

If the clamp is compressed, the handle may be released, resulting in the return spring being relaxed and returning the pusher tube and hence the slider, and the jaw parts being forced into the upward position by the cam being in engagement.

If the handle is completely released, the feed motion is automatically triggered by the pneumatic mechanism of the "Challenger Handle".

In this process, the valve of a gas cartridge is opened and an internal feed motion piston of the handle acts upon the feed rod with the axial movement and feed force. The feed rod moves toward the distal end and acts against the return spring force of a compression spring which is prestressed in the course of the feed motion. The spring has supported its one side on a shoulder of the feed rod.

The other side is supported by a spring support which is axially fixed on the shaft tube by corresponding lugs. Here, the feed rod extends through the spring support.

The feed rod which has been set in motion transfers the movement directly to the feed motion divider which is firmly connected to it, the latter having the function to divide the feed travel in two or more sections.

If the feed motion divider is in motion, it transfers the movement directly to the tongue which is firmly connected to it and picks up and entrains the most distal clip. Here, the tongue is passed through all the clips. Having covered a specific distance which is defined by a cam window in the metal feed motion plate and a cam on the feed motion divider, the metal feed motion plate also moves toward the distal end. This is why the stroke of the metal feed motion plate is always smaller than or equal to that of the tongue.

The metal feed motion plate which is set in motion picks up each individual clip one by one (incrementally) from their individual placement with the aid of the engaged feed lugs and causes them to move. The clips are now pushed toward the distal end and overcome the incrementally arranged retaining lugs of the metal retaining plate, wherein the clips are transported toward the distal end by one position at a time with each feed motion hub/delivery stroke.

At the same time, the most distal clip is pushed into the jaw by the tongue via the clip guideway.

If the full feed travel is achieved and all clips have arrived at their predetermined position, the feed rod or feed divider impinges on a stop, or in other words, the end of a groove in the feed rod impinges on a transverse cylinder pin, resulting in an increase of the force in the handle. If said force reaches approximately 40 N, while values of approx. 10 N, approx. 20 N, approx. 30 N, approx. 50 N, approx. 60 N and approx. 70 N (in each case ±5 N) are also conceivable, a valve in the handle is automatically opened which has the effect that the feed force falls to zero and the return stroke is initiated by the relaxation of the entire return spring in the shaft.

When the return stroke has been initiated, the feed rod is moved toward the proximal end. The feed motion divider which is firmly connected to the feed rod as well as the firmly connected tongue are directly pulled toward the proximal end. If the cam of the feed motion divider has covered the distance in the cam section of the metal feed motion plate, the metal feed motion plate is moved toward the proximal end as well.

In this process, the feed lugs are pulled over the clips/clamps which are displaced by one position. In case the clamps are entrained during the return stroke movement, the retaining lugs of the metal retaining plate which oppose said movement serve for holding them in place.

In the return stroke, the tongue is simultaneously retracted through the most distal clip and returns to the initial position. The return stroke movement ends if the feed motion divider hits the counterpart of the spring stop of the return spring.

Following said sequence, the clip applicator is ready to start the next cycle.

It has proven to be successful to dimension the outer tube with diameter values of 5.5 mm, 10 mm or 12 mm±10% in each case and with a length of 318 mm, with a variance of ±50% appearing to be reasonable.

The tongue or tongue lug is put through several clamps without providing any guiding function for these. It is realized as an elongated element with a pronounced buckling tendency for advancing and guiding the most distal clip with tolerances, but buckling is prevented by a lengthwise positioned flange and/or incorporated longitudinal beads. The tongue ensures safe gripping of the clamp/clip. It transfers forces onto the clamp with an angular and positional change. For compensating any tolerances, it is provided with a flexible tip, for instance made of a material with reduced thickness, or also with elasticity holes for instance in the form of cut-outs for reducing the bending cross-section. Any process of levering out the thrust lugs/pushing edges is prevented by a free zone in the form of a cut-out on the upper side of the tongue's tip. Due to the fact that the sheet metal protrudes beyond the tip of the tongue and rests on a support on the inner side of the clamp leg's fillet, a tissue protection is achieved and slipping off the tongue from the clamp web is prevented. This sheet metal element jutting out is referred to as a spacer or overhang.

The feed motion divider serves for a direct, firm mechanical connection to the drive train. This allows a feed motion hub or delivery stroke. The feed motion divider has a direct mechanical firm connection to the tongue. It has also a direct mechanical connection to the transport and entraining rail, but a loose one, i.e. a connection which is movable in one direction. This allows to subdivide a linear movement in two or more sections. It is useful to employ a cam which engages an elongated hole in a movable manner.

It is possible to do without the feed divider, but in that case one should make recourse to an integration in the tongue. Both the retaining rail and the transport and entraining rail/feed rail comprise lugs. The latter serve for safely gripping the clamps with small slippage and small tolerances. A low friction is desirable here. They serve for the guiding/supporting of components such as the tongue, for example. They serve for guiding the clamps and define a clip guideway which dictates the axial position of the clamps, wherein the clip guideway is exclusively defined by the tube's inner wall and the upper side of the metal retaining plate. The guiding of the metal feed motion plate is effected by the inner wall of the outer tube and by the packet formed by the clamps or, when the clamps are depleted, by the tongue which in turn is supported on the retaining rail. It is also conceivable to exchange the positions of the metal plates: Arranging the clips on the metal feed motion plate and supporting them on the tube's outer wall is plausible.

The following functions are fulfilled here:
Controlling the elasticity by the geometry of the lugs (minimizing the frictional forces) and
Controlling the guiding and supporting tasks by the geometry/height of the lugs.

Regarding the first control function, recourse is made to the following parameters: thickness of the sheet metal, width of the lugs and the cut-outs, position of beads and buckles, geometry of bends and positions of bending lines, sagittal geometry of the lugs, frontal and axial geometry as well as the incorporation of cut-outs for instance via elasticity holes. For the second point, the individually adapted geometry of the lugs, the mounting and supporting of the tongue by means of at least one lug, and the mounting and supporting of the sheet metal on the tongue by means of at least one lug is taken into consideration. Each of the lugs has a specific task. Some lugs may have a larger height than the others in order to protect the tongue. This means that the lugs do not all have the same height. This minimizes the friction. The aim is to achieve stiff guiding and transporting elements oriented in the longitudinal direction and configured so as to be elastic in the transverse direction.

Regarding the bridge on the retaining rail, it is to be mentioned that the retaining rail is assigned the function of a clip way/clamp guideway. It is designed such that the lug is supported on the upper jaw and is displaced by the latter in the course of a closure movement.

There are different ways of fixing the retaining rail on the outer tube, for instance by protrusions on the outer tube which project radially inwards, by suitable lugs and cut-outs in the retaining rail and/or lugs/protrusions and cut-outs on the outer tube, preferably in such a manner that a tensile force acts on the retaining rail during the return stroke, so that the retaining rail does not have to withstand any buckling load. A direct fixation of the retaining rail on the spring support is possible. An offset in fixation is also desirable (left-right-asymmetry), in order to increase the rigidity and for preventing a direct bending line. Providing the retaining rail with spring elements, which press it upwards toward the clip line/clamp line, acts as a compensation of tolerances.

There are also measures for stiffening the sheet metal for transferring a force with a low proneness to buckling. Skillfully placed beads and a defined edge collar would be suitable for this. The outer tube has supporting functions such as fastening the jaw, fastening the retaining rail, fastening a feed motion apparatus. It is preferably an integral, one-piece component with short tolerance chains. It may be produced in a single cutting operation in a single clamping process and with high accuracy.

The tube portion which is free of lugs fulfills a guiding function, namely the function of guiding the clamps on the tube wall, in particular while contacting the tube wall. A guidance of the sheet metal, the pusher tube, the feed motion divider and the metal retaining plate is also achieved.

The aforementioned lugs serve for fastening e.g. a metal retaining plate and can be used for positional fixation. They are elastic in their height, but also elastic in the lateral direction. As seen in the axial direction, they have small tolerances. As seen from one direction, they can be (unilaterally) joined. They can be manufactured by a (single) cut and a bending process.

BRIEF DESCRIPTION OF THE DRAWING FIGURES

Figure 2:
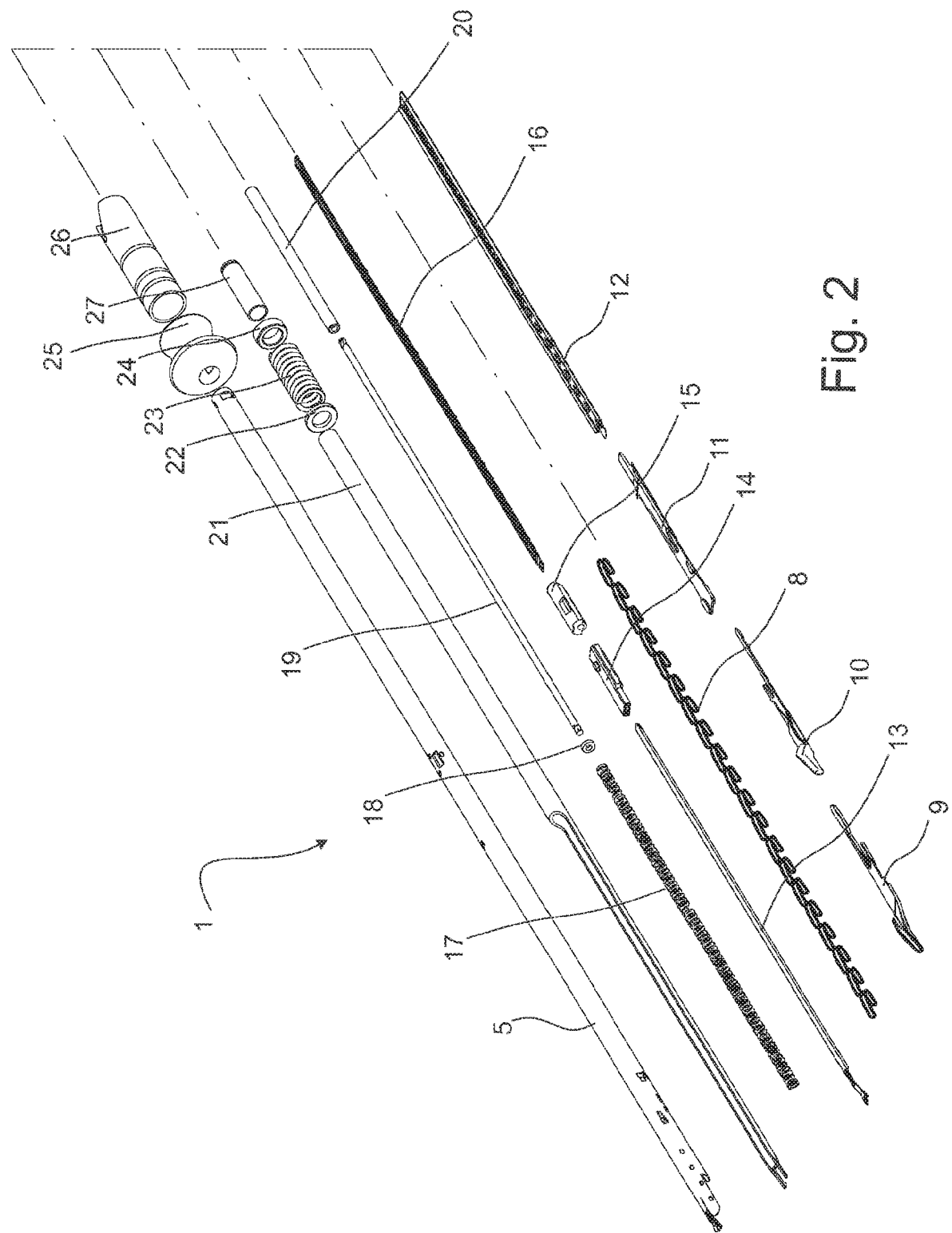
Figure 3:
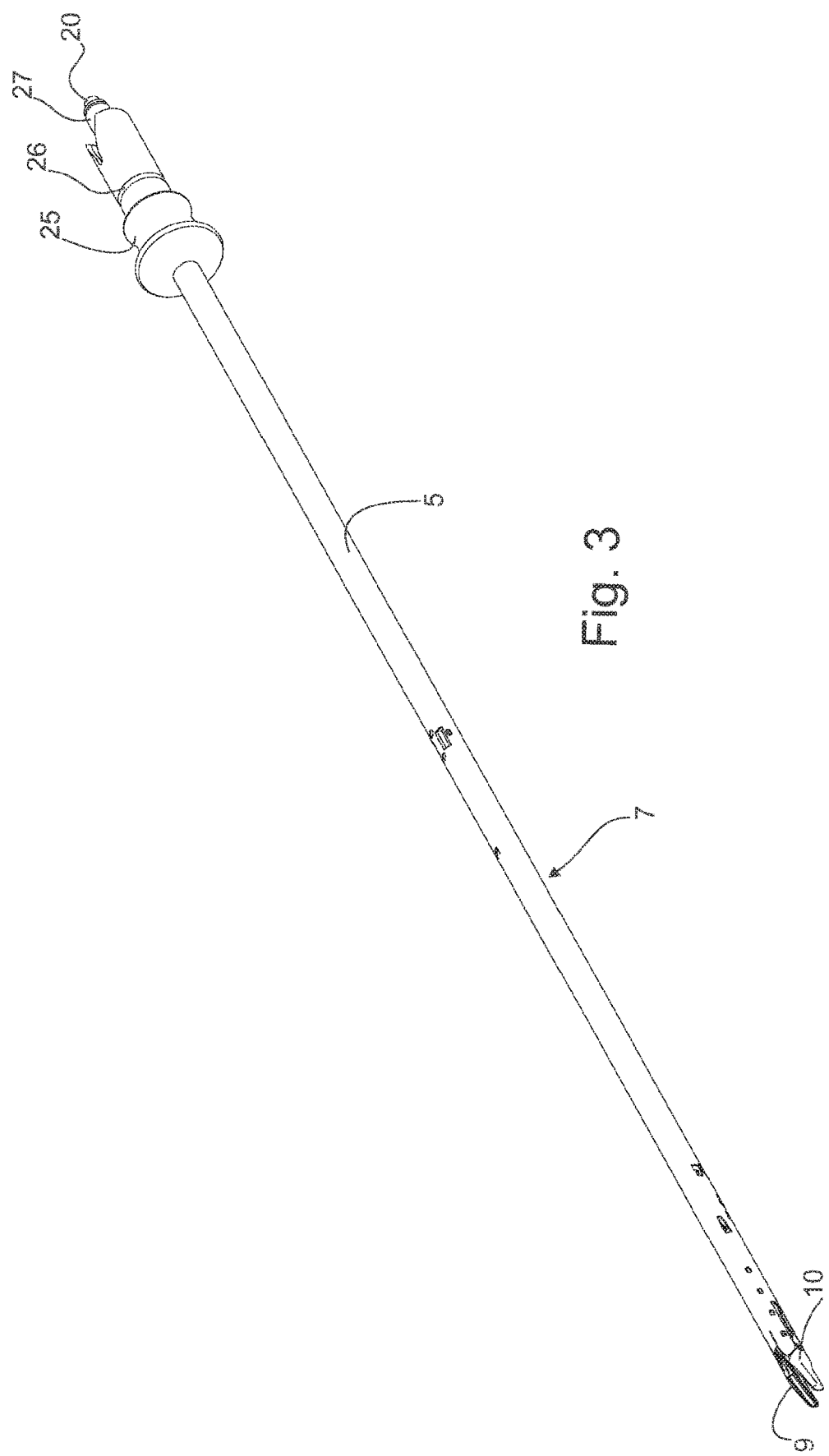
Figure 7:
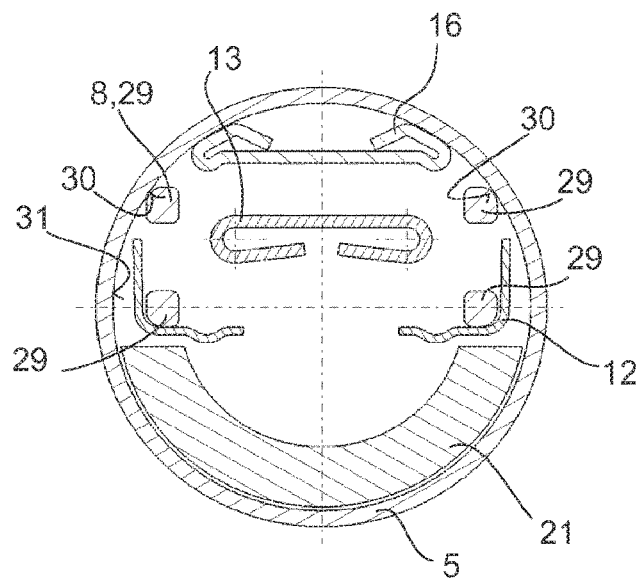
Figure 8:
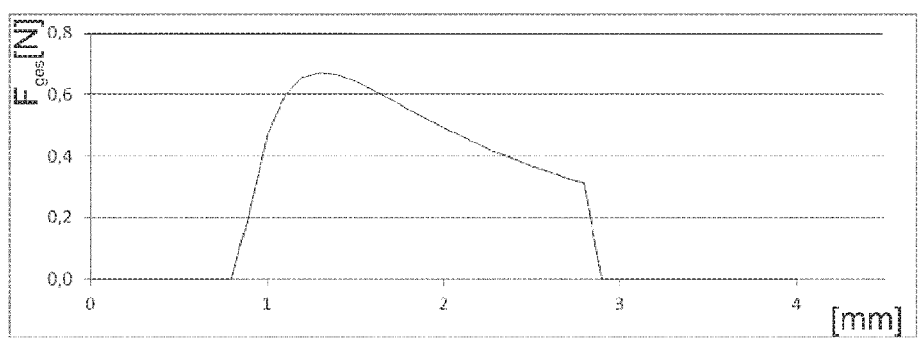
Figure 14:
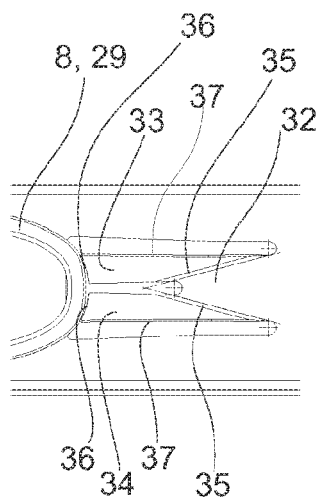
Figure 15:
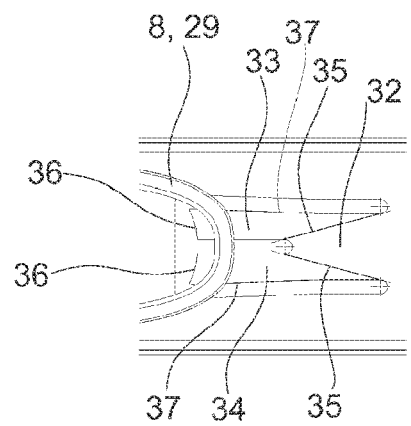
Figure 16:
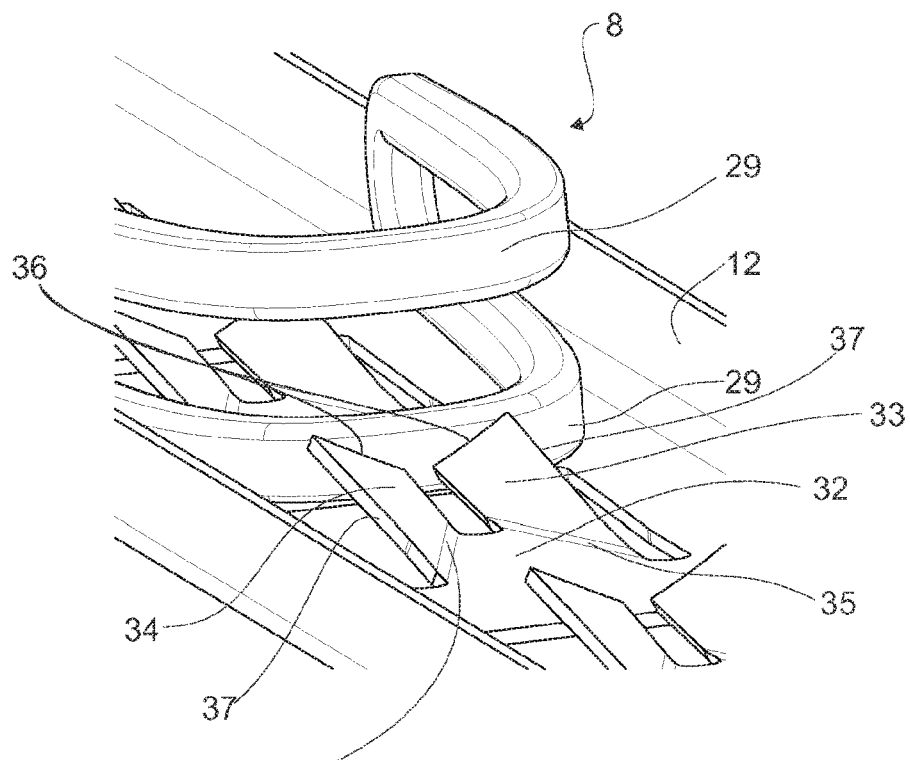
Figure 17:
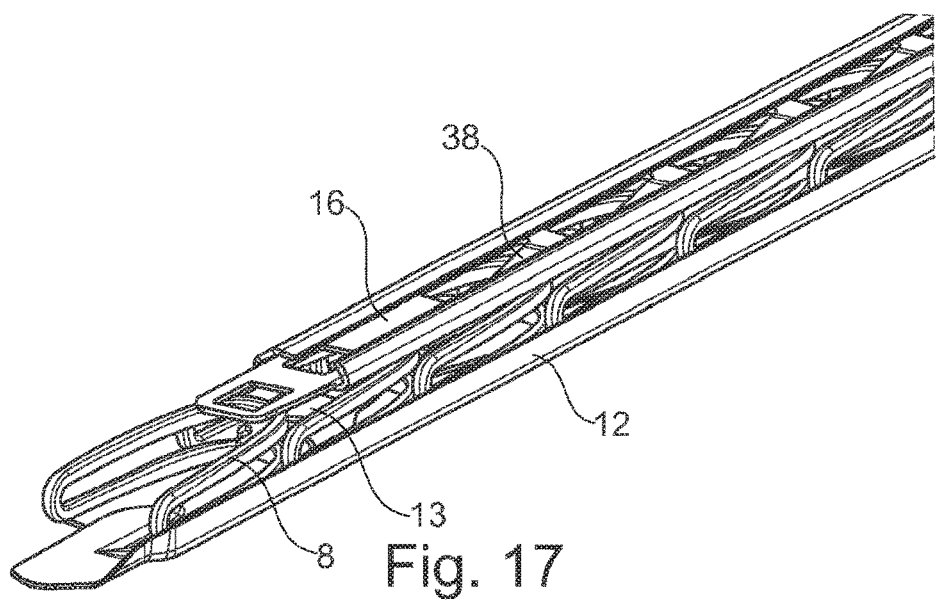
Figure 18:
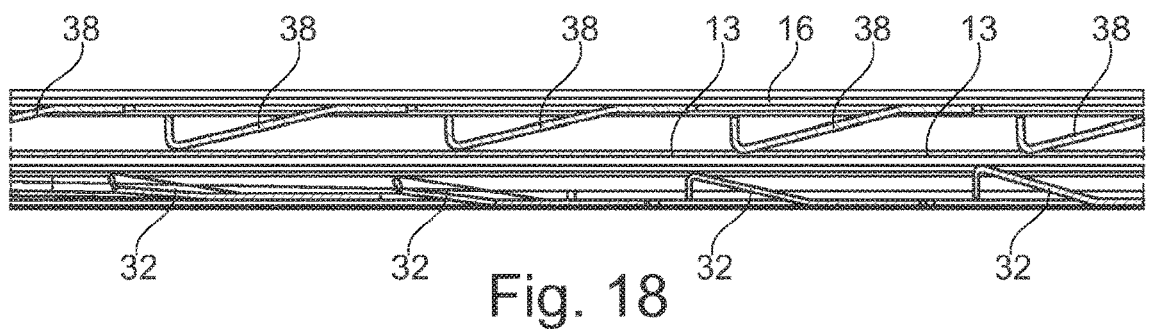
Figures 19, 20:
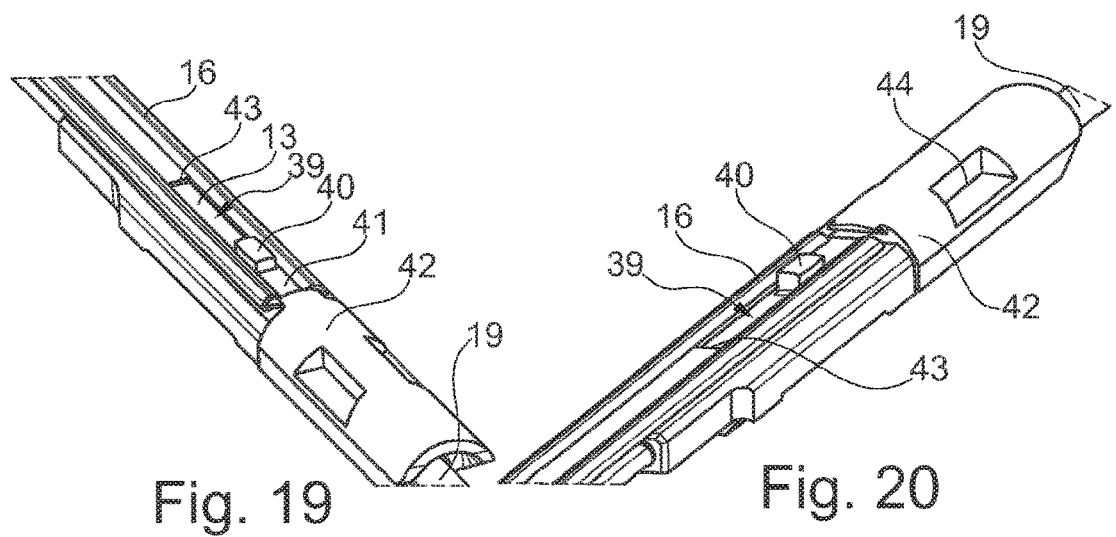
Figure 21:
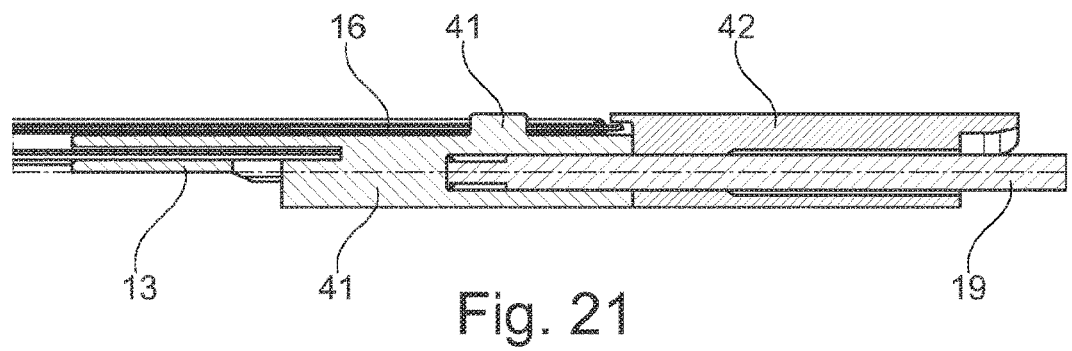
Figure 22:
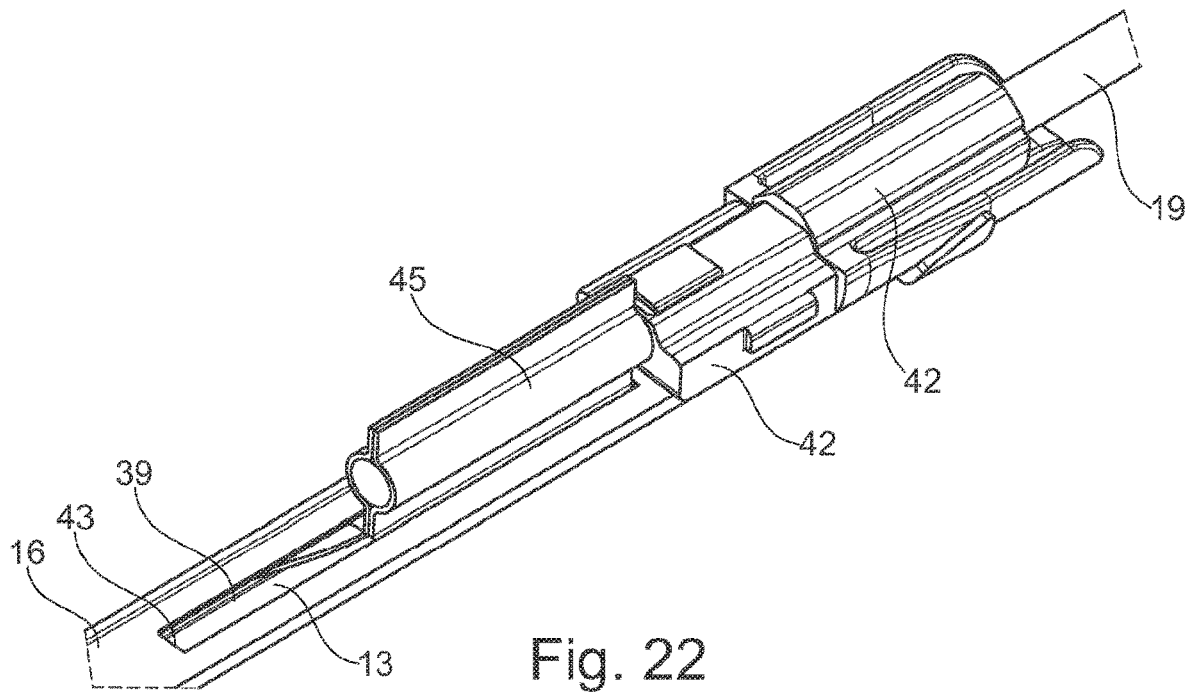
Figure 23:
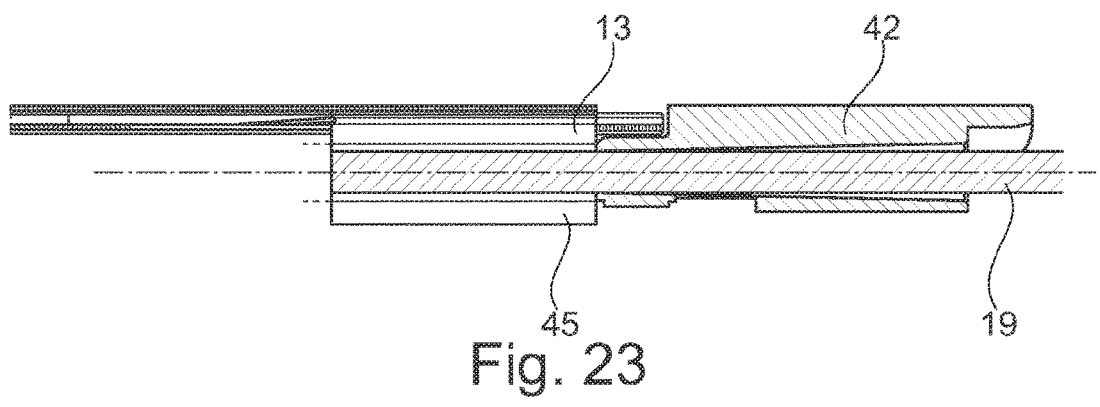
Figure 24:
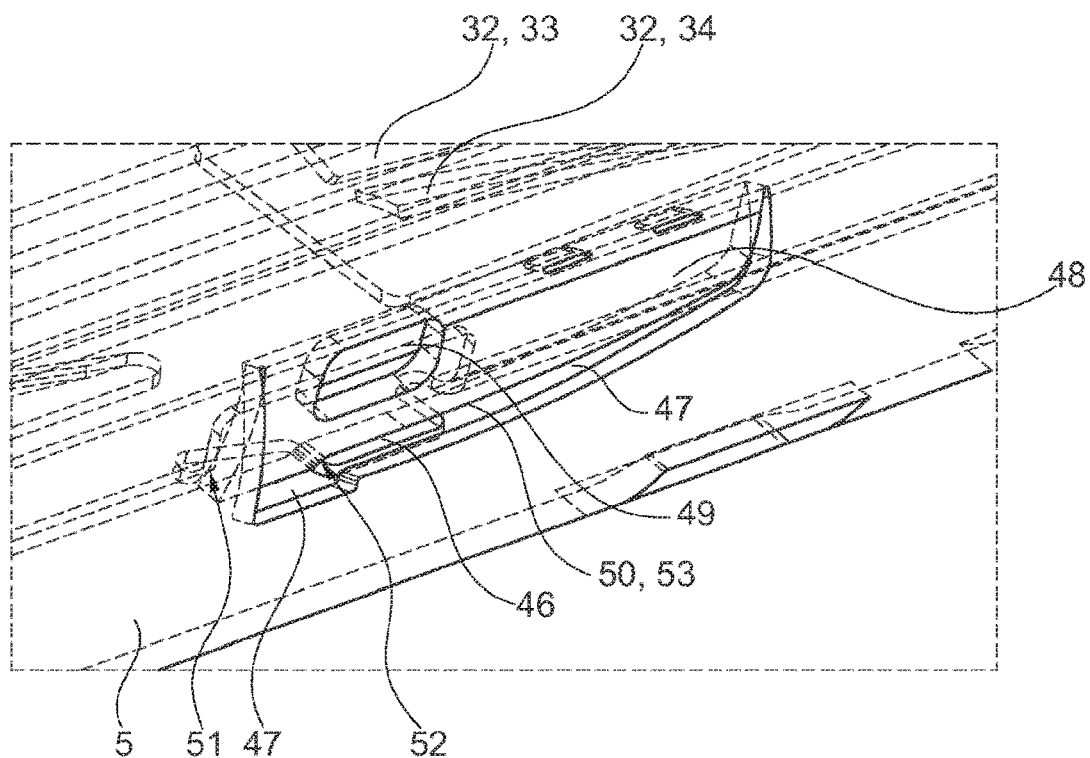
Figure 25:
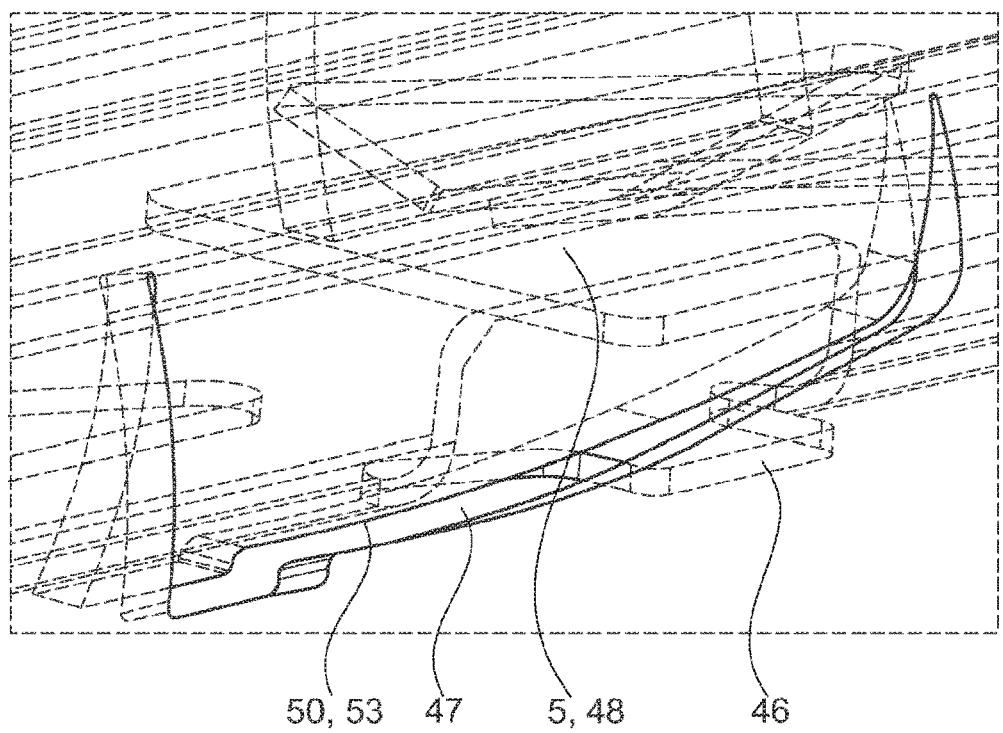
Figure 26:
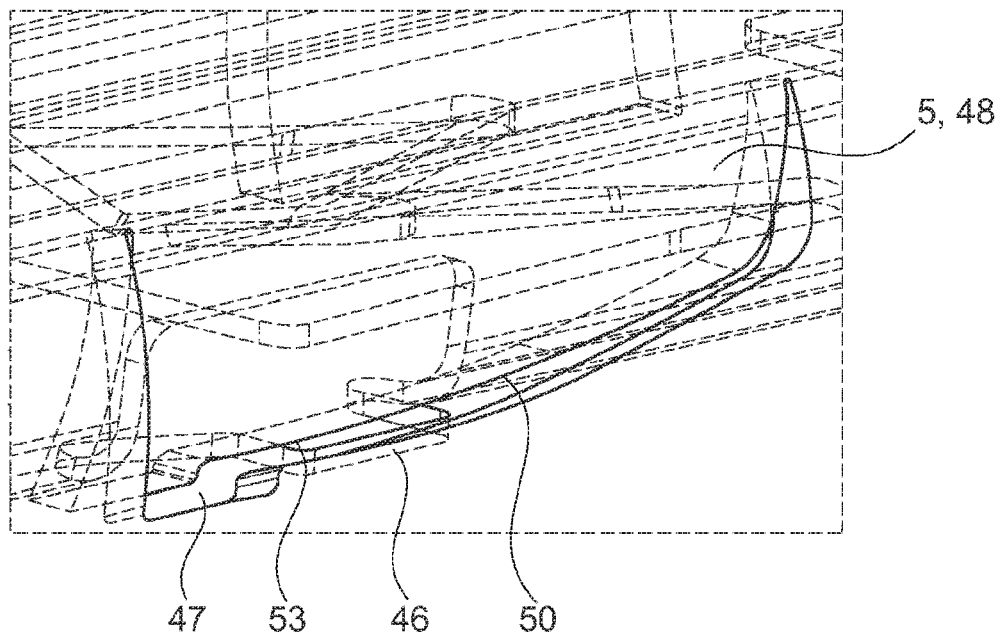
Figure 27:
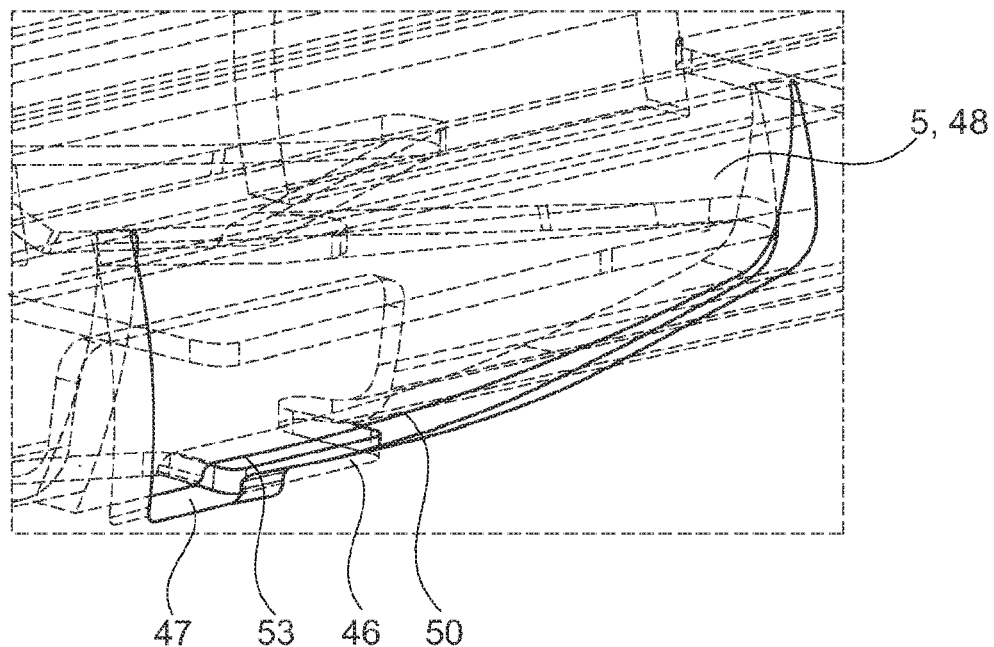
Figure 28:
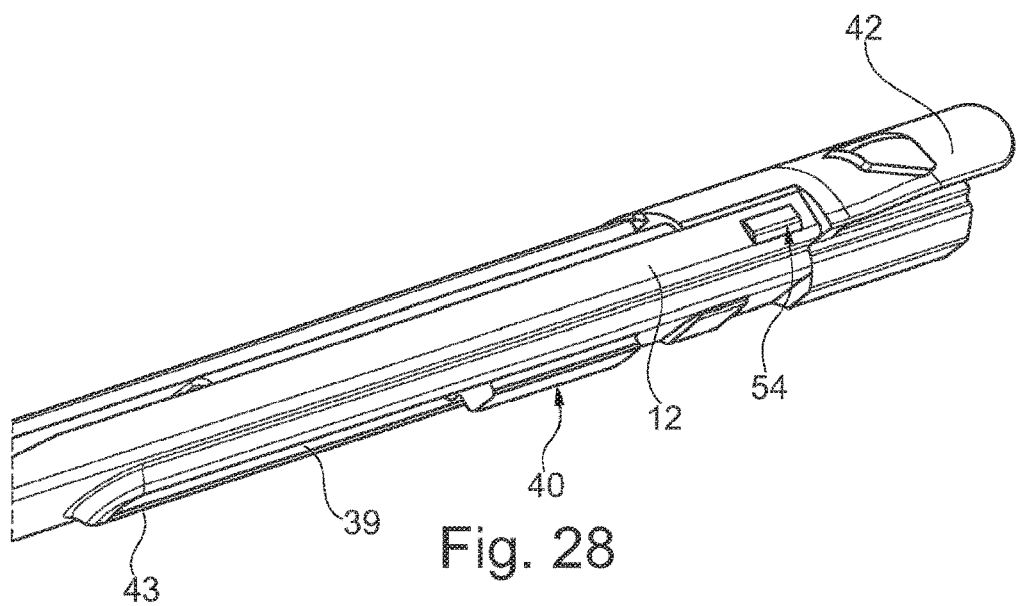
Figure 29:
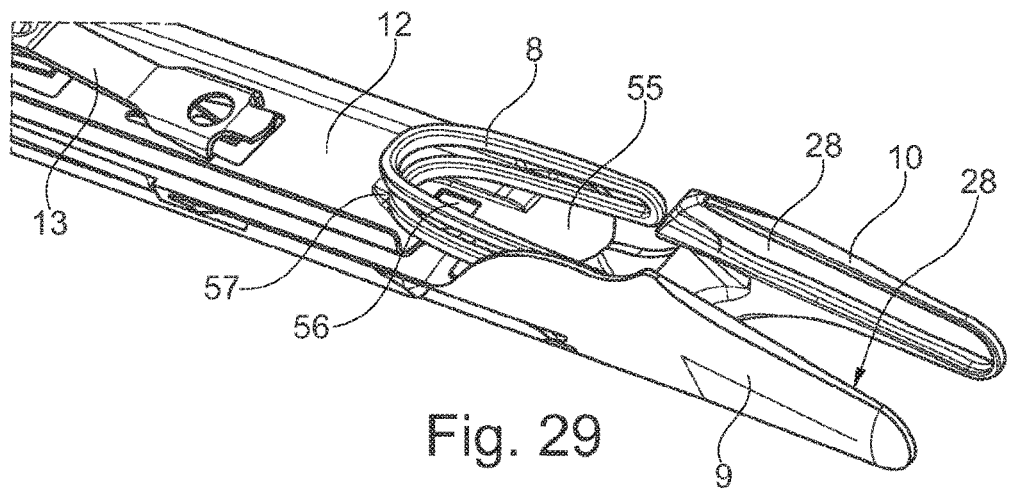
Figure 30:
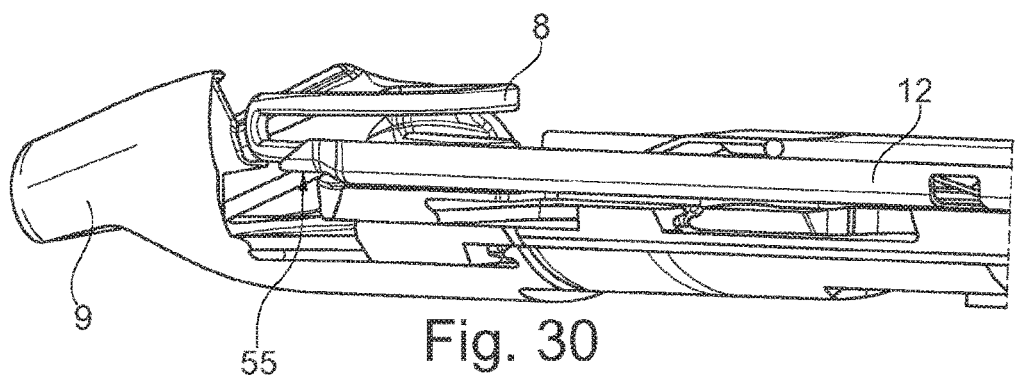
Figure 31:
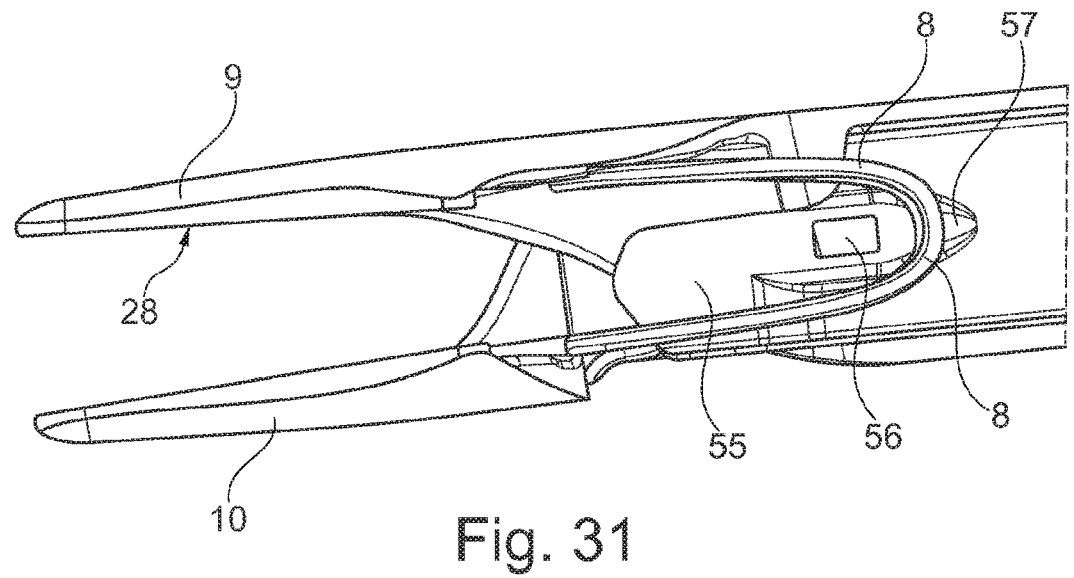
Figure 32:
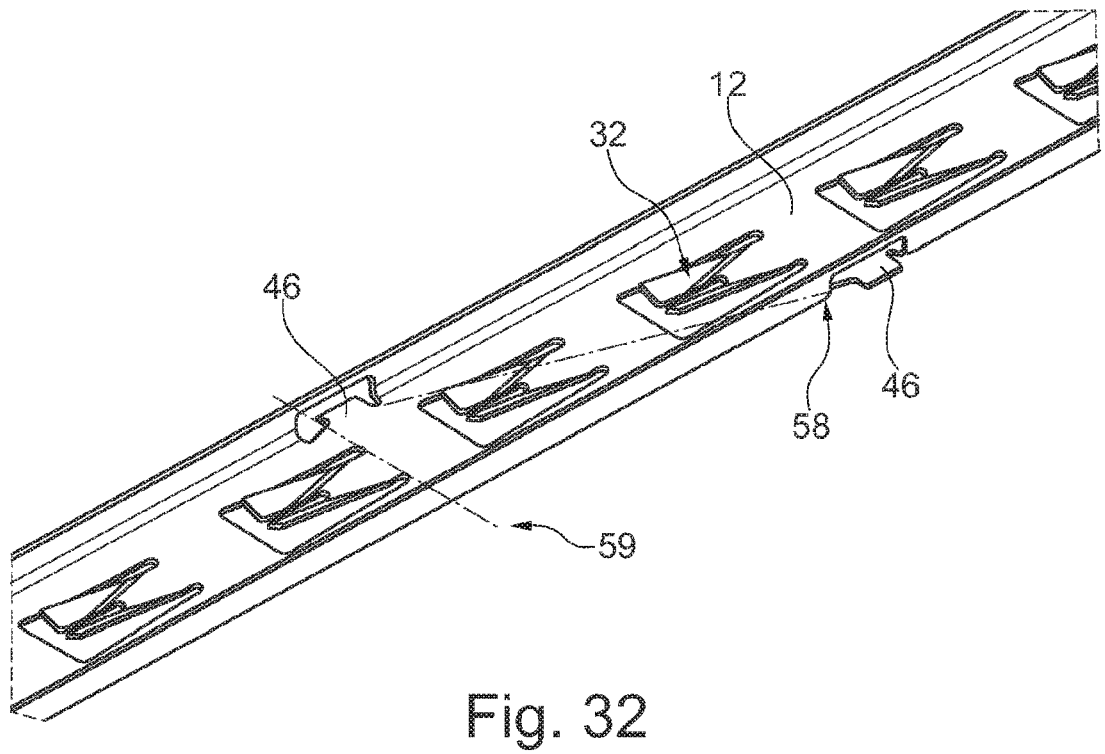
Figure 33:
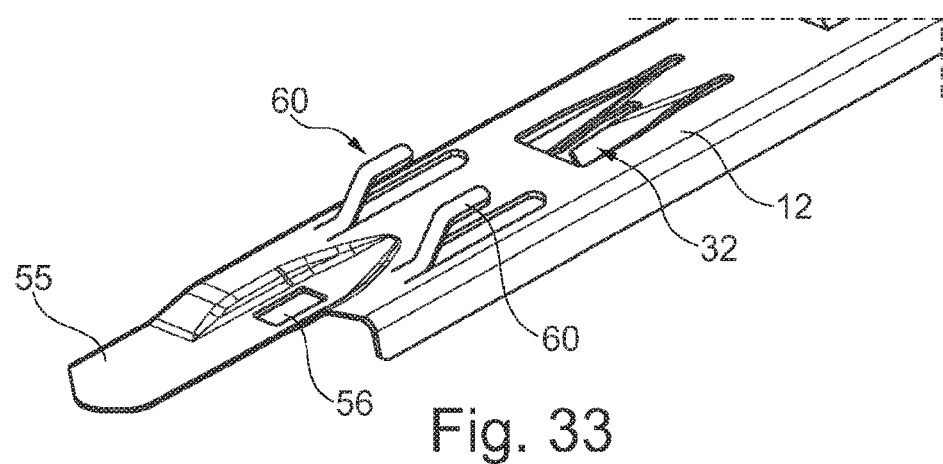
Figure 34:
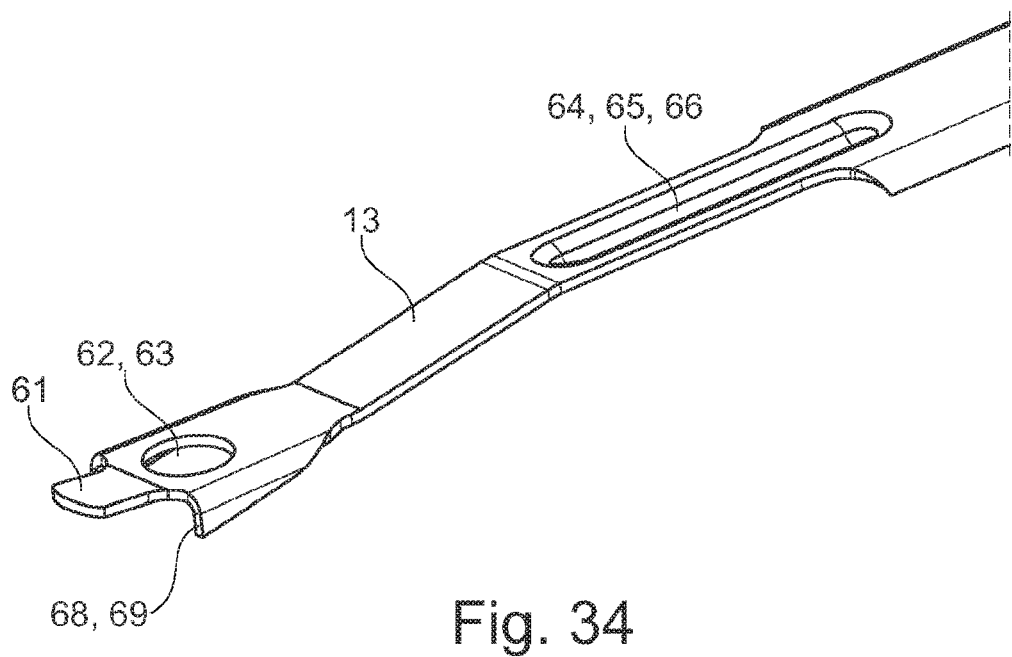
Figure 35:
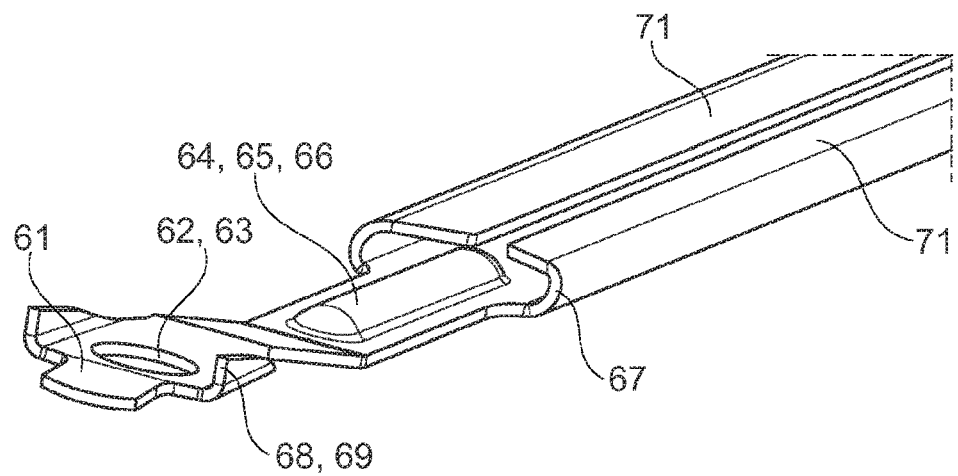
Figure 36:
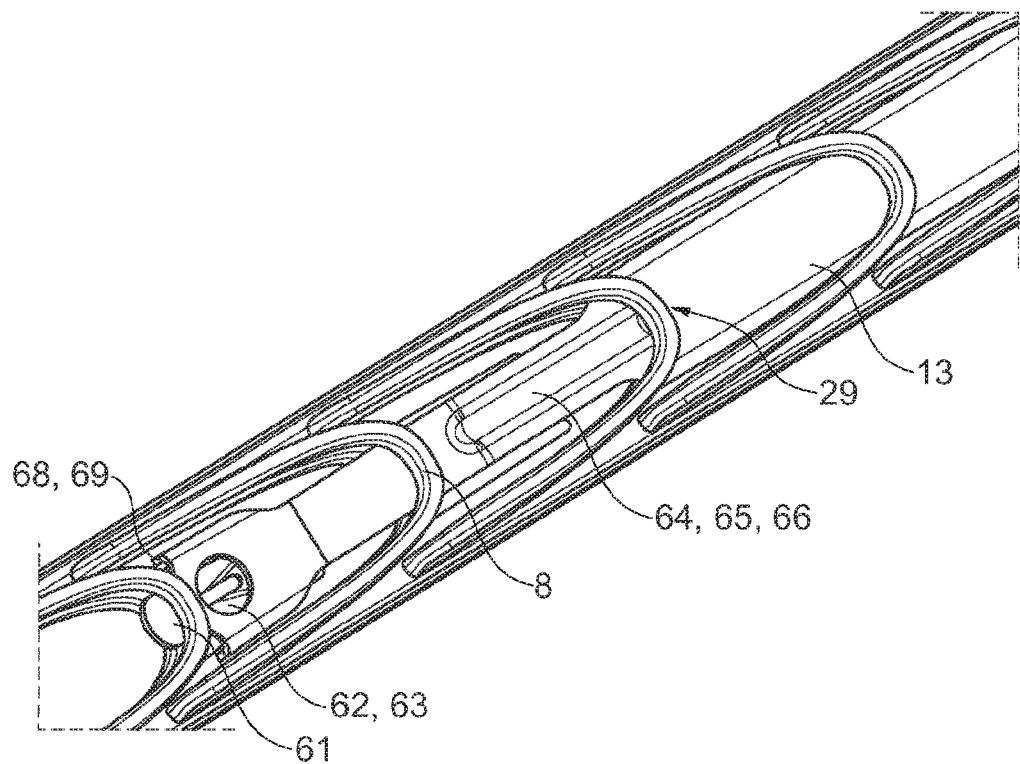
Figure 37:
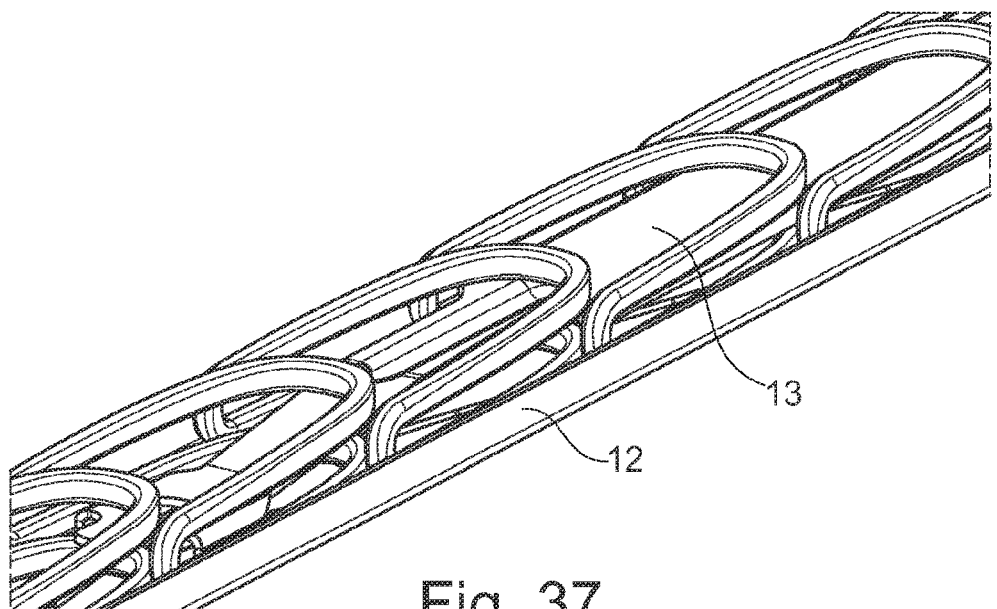
Figure 38:
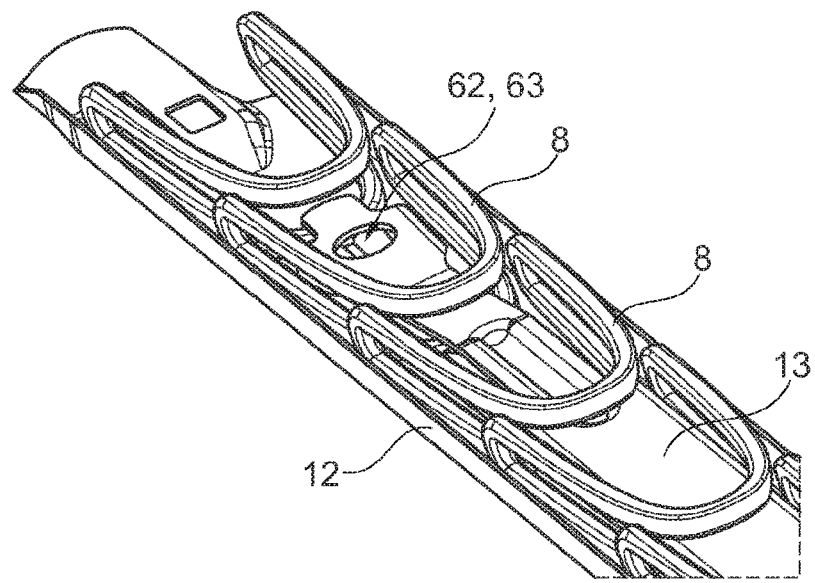
Figure 39:
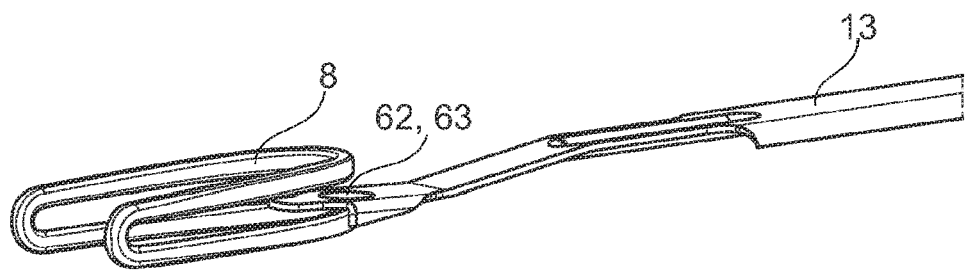
Figure 40:
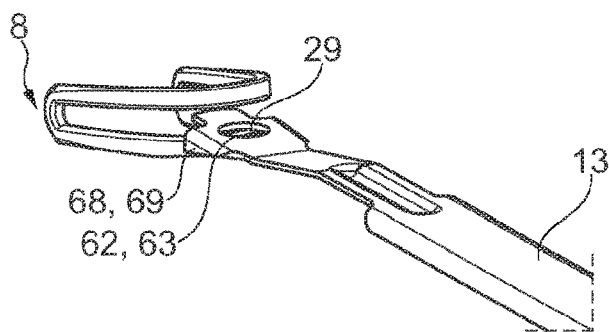
Figure 41:
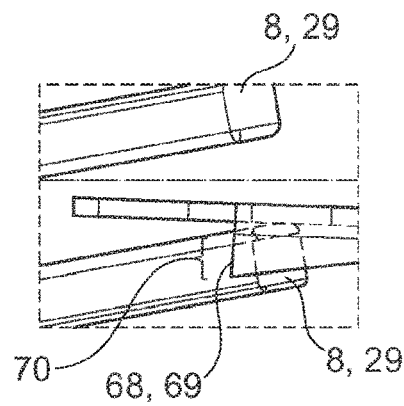
Figure 42:
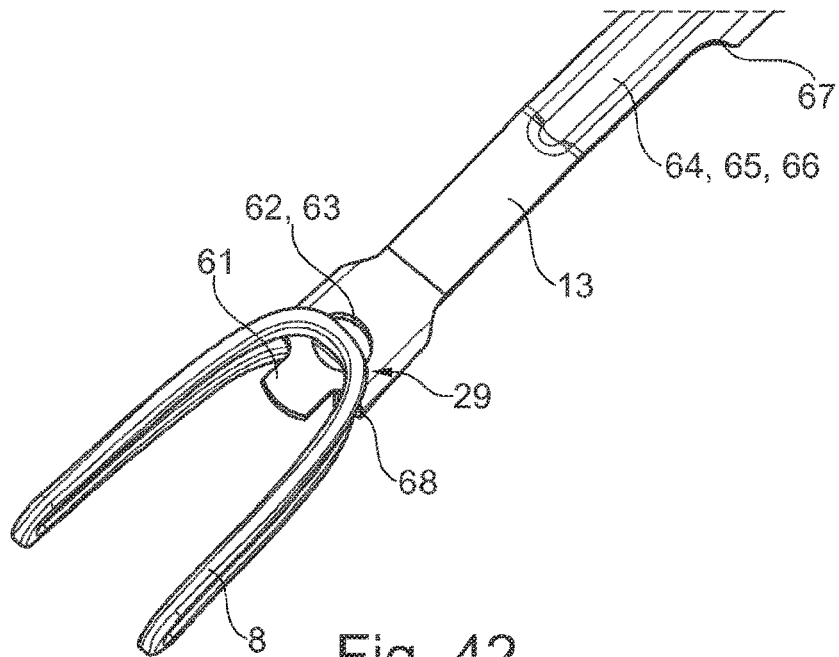
Figure 43:
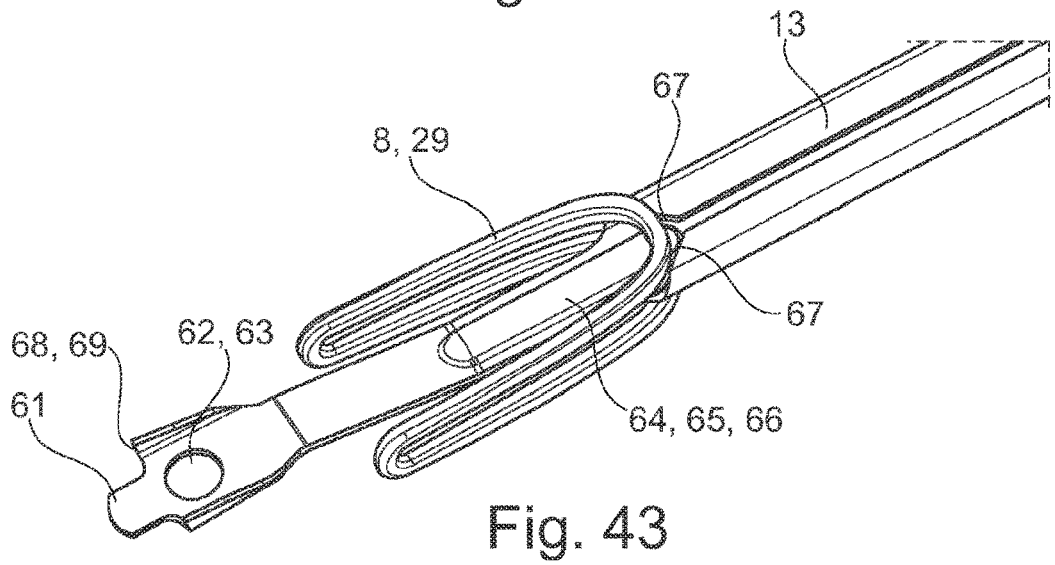
Figure 44:
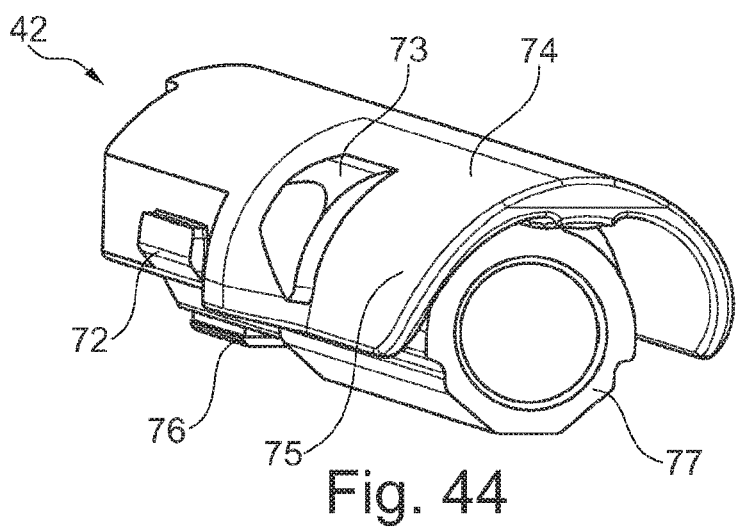
Figure 45:
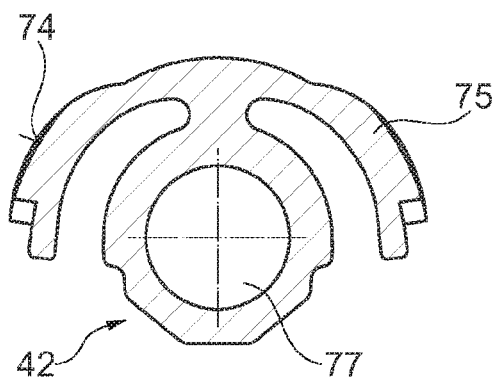
Figure 46:
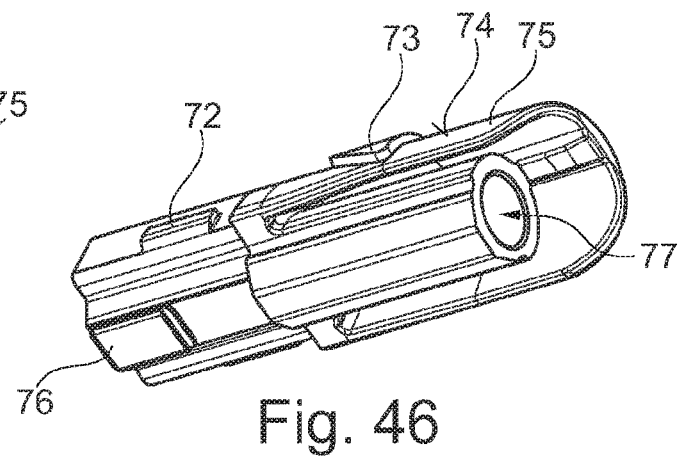
Figure 47:
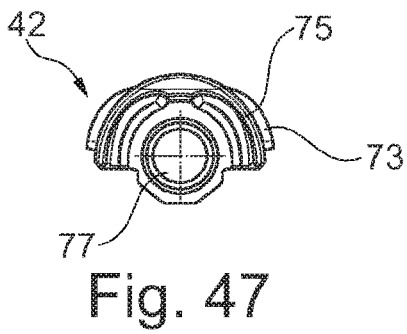
Figure 48:
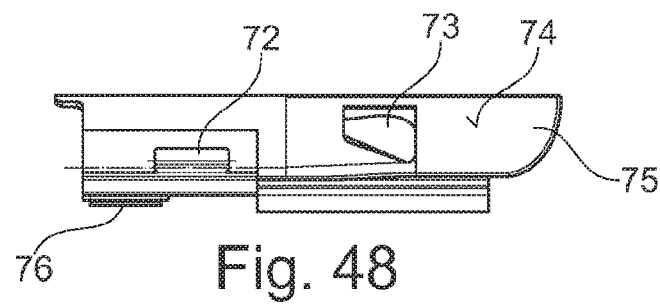
Figure 49:
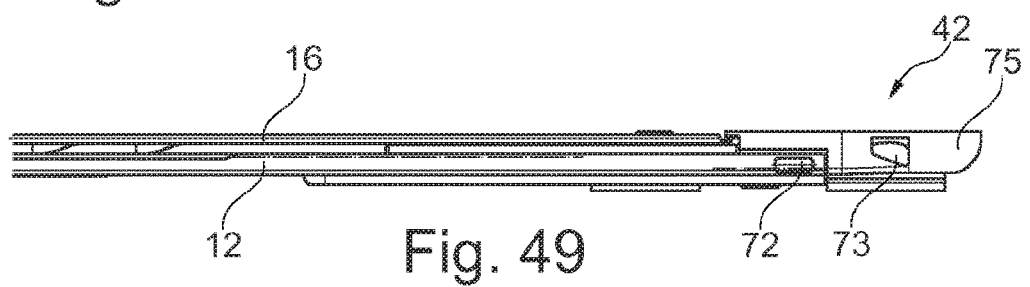
Figure 50:
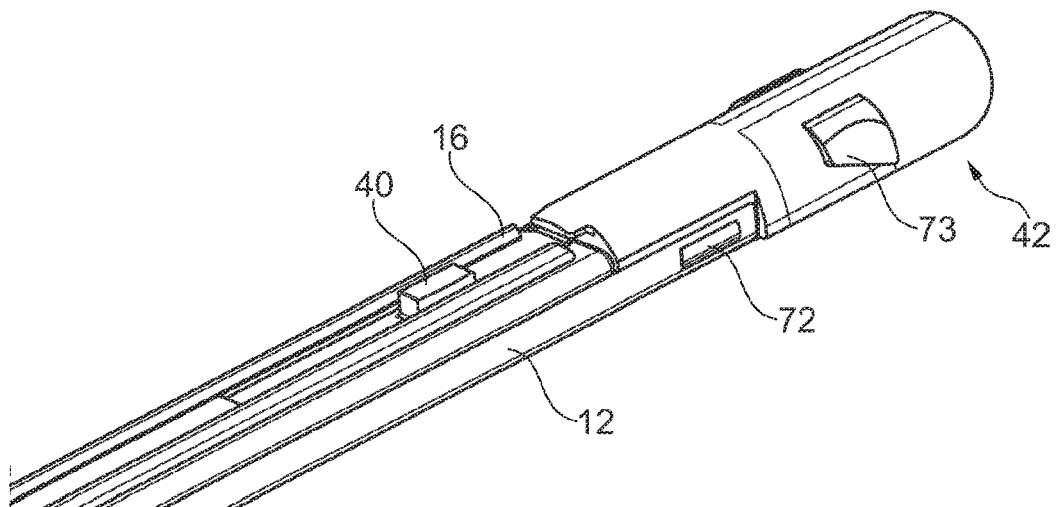
Figure 51:
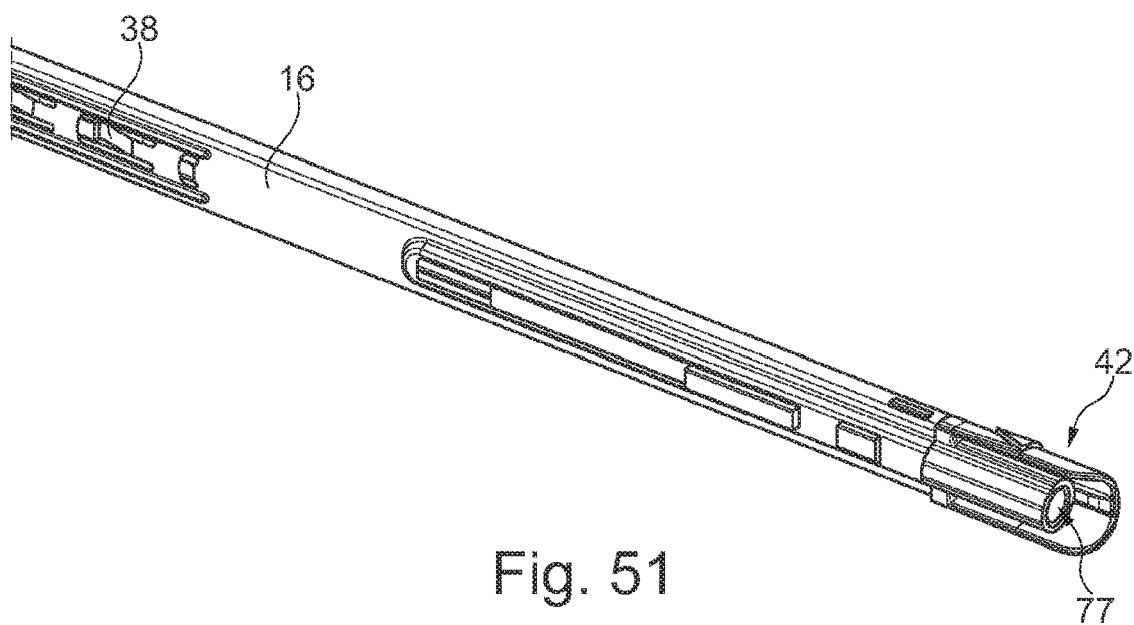

The invention will be explained below on the basis of drawings in which different exemplary embodiments are illustrated and in which:

FIG. 1 is a perspective illustration of an assembly unit of a medical shaft-type instrument according to the invention including a handle, FIG. 2 shows an exploded view of the medical shaft-type instrument of FIG. 1 in a perspective illustration without the handle included in FIG. 1, FIG. 3 shows the assembly unit of the individual parts of FIG. 2 in a perspective illustration, FIGS. 4 to 6 show perspective illustrations of only the distal tip of the medical shaft-type instrument of FIG. 1 without the outer tube, FIG. 7 shows a cross-section through an instrument shaft of the shaft-type instrument of FIG. 1, FIG. 8 shows a diagram for illustrating the force progression due to friction when a clamp able to be applied by the shaft-type instrument of FIG. 1 runs over a single, foldable form-fitting element such as a retaining lug or a clamp entraining element, FIG. 9 shows a diagram for illustrating the increase in force during "collecting" the clamps/clips during the feed motion, caused by a delivery stroke and during a return stroke, attributable to friction when the clamps run over the lugs, FIG. 10 shows an enlarged perspective illustration of a portion of a retaining rail including fastening protrusions and retaining lugs, FIG. 11 shows a further enlargement of a retaining lug of FIG. 10, FIG. 12 shows a top view of the retaining lug of FIGS. 10 and 11, FIG. 13 shows a retaining lug being in contact with a clamp designed as a double-web clip, in fact on the proximal side thereof, FIG. 14 shows the state of a retaining lug when the clamp has already run over it and in released position again, FIG. 15 shows a readjustment of a retaining lug in a position in which the clamp is about to run over it and has not released it yet, FIG. 16 shows a clamp contacting an erected and formed retaining lug abutting on the back of the clamp/clip for preventing a return motion of the clamp, FIG. 17 shows the assembly unit of a retaining rail storing a plurality of clamps in storage positions, the clamps being penetrated by a tongue and contacted by a transport and entraining rail from above, FIG. 18 shows a longitudinal section through the elements of FIG. 17, implementing a sandwich-like sheet metal packet and a clip stack/clamp stack with mutual support via lugs, FIG. 19 shows a perspective illustration of a first embodiment of a component for dividing the stroke, in the manner of a feed divider, FIG. 20 shows a rotated perspective illustration of the components of FIG. 19, FIG. 21 shows a longitudinal section through the components of FIGS. 19 and 20, FIG. 22 shows a second embodiment for realizing a division of the stroke, with integrated tongue, FIG. 23 shows a longitudinal section through the embodiment of FIG. 22 in the area of a feed divider, FIG. 24 shows a cut-out perspective illustration of an assembly unit made up of an outer tube and a metal retaining plate in mounted position, FIG. 25 shows the combination of the components of FIG. 24 in a position at the outset of the assembly process, FIG. 26 shows the components of FIGS. 25 and 26 at a point in time when the assembly process is already in an advanced stage, FIG. 27 shows the components of FIG. 25 at a point in time when the assembly process is about to be finished, as shown in FIG. 25, but enlarged, FIG. 28 shows a further exemplary embodiment for fixing the metal retaining plate via a spring support on a (not illustrated) outer tube using cut-outs, FIG. 29 shows a distal tip of the metal retaining plate with a clip/clamp stored near the tip, FIG. 30 shows a rotated illustration of the components of FIG. 29, FIG. 31 shows a view from the top to between two jaw part branches forming a jaw part area, a distal tip of the metal retaining plate serving as a (partial) cover in the manner of an abutment plate or bridge, FIG. 32 shows an illustration similar to FIG. 10 in the area of protrusions acting as mounting lugs, defining an asymmetrical bending line and avoiding a direct bending line, FIG. 33 shows a bottom illustration of the metal retaining plate in a perspective form for visualizing spring lugs provided there, FIG. 34 shows a distal end region of a tongue/feed tongue comprising a notch functioning as an insertion opening, FIG. 35 shows a view in perspective form from the bottom to the distal tip of the tongue of FIG. 34 comprising a pilot bead in the manner of a deflector, acting as a movement-guiding element and increasing the flexural rigidity, FIG. 36 shows a partial illustration of the clamps, the metal retaining plate and the tongue in the area of the pilot bead, FIG. 37 shows an illustration of the components of FIG. 36 in a slightly rotated form, FIG. 38 shows an illustration of the components of FIGS. 36 and 37 in a perspective form as seen from behind, FIG. 39 shows the engagement of the tongue on the most distal clamp, FIG. 40 shows the components of FIG. 39 in a perspective illustration as seen from behind, FIG. 41 shows an enlargement of the contact area between the clamp and a pushing edge/thrust lug of the tongue, FIG. 42 shows the clamp upon entering the insertion opening of the tongue in a perspective illustration as seen from above, FIG. 43 shows a clamp when conveyed along the tongue toward the distal tip region of the tongue, FIG. 44 shows the spring support in a perspective illustration, FIG. 45 shows a cross-section through the spring support in the area of sealing surfaces, FIG. 46 shows a perspective illustration of the spring support of FIGS. 44 and 45 as seen from below, FIGS. 47 and 48 show a side view and a front view of the spring support of FIGS. 44 to 46, FIG. 49 shows a side view of the spring support of FIGS. 44 to 48 with a metal retaining plate mounted thereto and a transport and entraining rail coupled thereto, FIG. 50 shows the spring support when clipped in place in a metal retaining plate, and FIG. 51 shows an illustration of the components of FIG. 50 with a view onto a free zone (elongated hole with stroke limitation) for the feed divider with the metal retaining plate being clipped in place in the spring support.

The Figures are merely of schematic nature and serve exclusively for the understanding of the invention. The same elements are provided with the same reference symbols. Features of the individual exemplary embodiments are interchangeable. Hence, such features can be exchanged among themselves.

DETAILED DESCRIPTION

FIG. 1 illustrates a first embodiment of a medical shaft-type instrument 1. It comprises an instrument handle 2 on its proximal end. In brief, the instrument handle 2 may also be referred to as a handle. The handle may be designed in the manner of a "Challenger Handle". An instrument head 3 is formed on the distal end of the medical shaft-type instrument 1. Arranged between the instrument handle 2 and the instrument head 3 is an instrument shaft 4 connecting the two components to each other.

The instrument shaft 4 comprises an external outer tube 5. The outer tube 5 may have an annular cross-section and be formed in the manner of a hollow cylinder. The instrument handle 2 acting as a contact area for a hand forwards an instruction of an operating surgeon to the instrument shaft 4 in order to actuate the instrument head 3 by means of it. A clip magazine 7 is present within the outer tube 5 functioning as a housing 6. The clip magazine 7 is a magazine for storing clamps, clips, brackets or other clamping configurations suitable for ligature use. Such clamps, in particular ligature clamps or clips are provided for being plastically deformed or locked in place, in order to stanch an organ of a mammalian, for instance a blood vessel of a human, in the deformed state.

A plurality of such clamps 8 is represented in FIG. 2.

FIG. 2 shows the individual parts of the medical shaft-type instrument 1, without the instrument handle 2. In particular, an upper jaw part/an upper jaw part branch 9, a lower jaw part/a lower jaw part branch 10, a slider 11 which may be referred to as a cam carrier component and a retaining rail 12 can be seen.

In the embodiment illustrated there, twenty clamps 8 are utilized in total. It would also be possible, however, to use a higher or smaller number of said clamps 8. A tongue 13 which may also be referred to as a feed tongue, a feed divider 14, a spring support 15 and a transport and entraining rail 16 which may also be referred to as a feed rail, are also included. Further, a feed spring 17, a sealing disc 18, a feed rod/pusher rod 19 and a feed rod end piece 20 are used. A pusher tube 21 adjoins a sealing ring 22. The sealing ring 22 is a distal limitation of a compression spring 23 which is adjacent to a spring flange 24. The compression spring 23 is supported on the spring flange 24. The compression spring 23 is responsible for a return motion of the jaw parts 9 and 10, hence for moving the upper jaw part 9 away from the lower jaw part 10.

The components 9 to 24 are provided for being inserted within the outer tube 5. The outer tube 5 is inserted in a handle flange 25 after the assembly process. The handle flange 25 for its part is in a force-fitting, form-fitting and/or material-bond type contact with a handle piece/handle coupling component 26 in order to connect to the instrument handle 2. A hollow cylinder end piece 27 is arranged proximally with respect to the spring flange 24. Said hollow cylinder end piece 27 as well as the feed rod end piece 20 can be seen as proximally protruding from the handle piece 26.

FIG. 3 illustrates the components known from FIG. 2 in the assembled state.

FIGS. 4 to 6 suggest the assembly unit made up of the upper jaw part branch 9 and the lower jaw part branch 10 for receiving the most distal clamp 8 within a shell form 28. A retaining rail 12 formed as a metal retaining plate is arranged below the transport and entraining rail 16.

FIG. 7 allows to clearly see the guidance of the clamps 8 in a cross-sectional view. As can be seen, the clamp 8 illustrated there has its four clamp webs 29 supported on the retaining rail 12 as well as on the outer tube 5. The clamp webs 29 may be briefly referred to as webs.

In this arrangement, the outer tube 5 comprises contact surfaces/abutment surfaces 30 for contacting the upper clamp webs 29 of the clamp 8. The clamp 8 is designed here in the manner of a double-web clip. The tongue 13 is provided for ejecting the foremost, first clamp 8, i.e. the most distal clamp 8, whereas the transport and entraining rail 16 is provided in the manner of a metal feed plate for moving all the clamps 8 in the clip magazine 7. The contact surfaces/abutment surfaces 30 are designed such that they allow a sliding motion of the clamps 8 along it.

Optionally, but not illustrated, the outer tube 5—in the area of the contact surface 30 intended for being contacted by the clamp webs 29—may be provided with recesses such as slots, grooves, serrations or through-holes, through which the clamps 8 may project outwards to the outer side of the outer tube 5, i.e. so as to penetrate the outer tube 5. This allows to achieve a particularly compact configuration of the shaft-type instrument 1.

The clamps 8 also rest on the retaining rail 12 with their clamp webs 29, in fact in such a manner that a compression/deflection of the clamps 8 is forced in cooperation with the support on the outer tube 5. The clamps 8 do not contact each other here. The tongue 13 is fed through the double-web clip-like clamps 8, resulting in a sort of threading of the clamps 8.

In this arrangement, the clamp webs 29 form leg portions. The feed motion of the clamps 8 is effected by a forward and rearward movement of an elongated component comprising lugs in the style of protrusions, lamellas or barbs. The clamps 8 are exclusively guided on an inner wall 31 of the outer tube 5 and on a sheet-metal type retaining rail 12. This results in an effective use of the installation space. Noises, in particular rattling noises, are prevented. This results in a precise guidance. A compensation of the tolerances is achieved as well. A separate channel is not required.

A channel-like construction as shown in FIG. 7 is sufficient here, and the use of metal sheets has advantages in terms of dimensioning the stiffness.

The retaining rail 12 comprises retaining lugs 32. These can be clearly seen in FIGS. 10 to 16, for instance. In said Figures, a butterfly-type segmentation of the retaining lugs 32 into a first retaining lug portion 33 and a second retaining lug portion 34 can be seen as well. Thus, these two retaining lug portion 33 and 34 constitute a kind of butterfly lug. The wings of a butterfly lug may also be referred to as first and second retaining lug portions 33 and 34.

The clamp webs 29, which may also be designated as legs, slide/slip over the retaining lug portions 33 and 34 and result in the retaining lug portions 33 and 34 folding along a swivel or bending line 35. The swivel or bending line 35 may also be referred to as a bending axis or swivel axis.

As can be clearly seen especially in FIGS. 13 and 16, a movement of the clamps 8 in proximal direction is prevented by a proximal end of the clamp 8 resting against a distal edge 36 of the retaining lug 32. As can be clearly taken from FIGS. 10 and 16, the shape of the lugs is also implemented in a butterfly-type shape. The protruding lugs including wings having the largest possible edge/area for supporting the clamps 8 on the clamp's back should offer a high rigidity. The geometry of the retaining lugs is designed such that it can get out of the way during the run-over process, without going below the level of the metal sheet. In other words, the retaining lugs 32 lay down flat. In the erected state, side edges 37 of the retaining lugs 32 form lines which are almost parallel. They extend predominantly in the longitudinal direction. At least an angle from proximal larger than 0° is acceptable. This provides for minimum friction. If the clamp 8 runs over the retaining lug 32 from proximal, this angle will be enlarged.

With a lookahead to FIG. 18, it is mentioned that also the transport and entraining rail 16 comprises lugs, namely clamp entraining elements or clamp entraining lugs 38. Increments and distances of the lugs are important for the limitation of the length of the component, in particular for the length of the magazine. They dictate the work of friction. They have to be arranged in a skillful way with respect to their position in relation to the feed hub which may also be referred to as a delivery stroke. They can be formed in a simple manner if a shaped metal strip or a plastic component is used as a starting base for them. They should be arranged preferably in the style of springy lugs with precisely defined distances. The mutual distances between the retaining lugs 32 may be variable along the length of the sheet metal, i.e. does not have to be kept constant. The distances of the clamp entraining elements/lugs 38 relative to each other should also be variable along the length of the sheet metal, i.e. should not remain constant.

The spacing increments of the lugs should be selected such that a sequential collecting of the clamps 8 is carried out starting from a rest position of the clamps 8, resulting from non-constant distances. This has the effect of a continuous increase of force. In that case, a predetermined amount of a force to be applied will not be exceeded. The spacing increments of the lugs should be selected such that the length of the magazine is minimized. The spacing increments of the lugs are selected here such that the collecting process occurs sequentially from distal to proximal depending on the rest position of the clamps in order to avoid a mutual collision of the clamps or counteract it. The following relationship is suitable for the determination of the spacing A:

The spacing (A) is referred to as the spacing between the $j^{th}$ and the $(j-1)^{th}$ lug either of the retaining rail 12 or of the feed rail/transport and entraining rail 16, with j specifying the position of the lug starting from distal and n corresponding to the total number of the clips in the applicator.

Spacing of the retaining lug (ARHL)=constant spacing (AK)+incremental spacing RHL (AjRHL)

Incremental spacing RHL (AjRHL)=increment RHL IKRHL·(n−j)

Spacing of the feed lug (AVSL)=constant spacing (AK)+constant (K)+incremental spacing VSL (AjVSL)

Incremental spacing VSL (AjVsL)=increment VSL IKVSL·(n−j)

However, the constant spacing (AK) depends on the clamps, their size and their geometry and amounts to approximately 8.5 mm, for example. It is also possible to provide a constant increment (iK) and a variable increment (iV). The total increment I is then calculated as follows: I=IK+IV. This allows to determine the location of the occurring maximum force and hence the buckling of the sheet metal.

FIG. 8 illustrates the friction-related behavior as a function of the position where the clamp 8 runs over one of the lugs 32 and 38. The abscissa shows the length of the lugs in mm, whereas the ordinate shows the total force $F_{ges}$ in Newton.

In FIG. 9 is an illustration of the increase in force during "collecting" the clamps 8 in the course of a delivery stroke, on the one hand, and in the course of a return stroke on the other hand, due to the friction when all the clamps 8 run over all the lugs (retaining lugs 32 and clamp entrainment lugs 38). Here, the solid line represents the increase in force/force progression during the feed motion/delivery stroke, and the broken line represents the increase in force/force progression during the return stroke. The abscissa shows the feed travel in mm, whereas the ordinate shows the need of physical force in Newton.

Returning to FIGS. 17 and 18, reference is made to the sandwich-like arrangement of the transport and entraining rail 16 above the tongue 13 which for its part is situated above the retaining rail 12. Thus, the retaining rail 12, the transport and entraining rail 16 and the tongue 13 are arranged one above the other and so as to be axially movable. The lug heights of at least some of the lugs 32 and/or 38 are dimensioned here such that they guide the tongue 13 situated in the middle.

In consideration of the FIGS. 19 to 21, it should be obvious that it is desirable to achieve a feed motion division by means of an elongated hole 39 which is engaged by a cam 40. The cam 40 protrudes from a feed divider 41 which may be designed so as to be separate from a spring support 42. The cam 40 may be an integral constituent part of the spring support 42. In any case, the feed rod 19 extends through the spring support 42 and is connected to the feed divider 41 in an axially fixed manner. The cam 40 of the feed divider 41 extends through the elongated hole 39 of the transport and entraining rail 16. The tongue 13 is connected to the feed rod 19 in an axially fixed manner, so that any movement transferred from the feed rod 19 is directly imparted to the tongue 13 and passed on to the transport and entraining rail 16 not until the cam 40 impinges on a stop edge 43. In this way, two engaging components are configured such that a pin, a cam or any other protrusion engages in a hole, a groove or a recess such that an axial relative movement of the two parts with respect to each other by a specific amount is allowed, but a combined movement is caused upon reaching a stop.

As can be seen particularly well in FIGS. 19 and 20, the spring support comprises recesses 44 which can be engaged by protrusions or lugs of the outer tube 5 in order to bring about an axial fastening.

The FIGS. 22 and 23 show a variant differing therefrom, namely a variant in which the pusher rod 19 is directly connected to the tongue 13. To this end, the tongue 13 is crimped around a distal end of the pusher rod 19 in the manner of a folded sheet. It goes without saying that the tongue 13 may also be an integral constituent part of the pusher rod 19. With the configuration of FIGS. 22 and 23, there is no separate feed divider 41. However, said folded sheet 45 which provides for the connection between the tongue 13 and the pusher rod 19 vertically engages an elongated hole 39 provided in the transport and entraining rail 16, in order to come in contact with a stop edge 43—similar to the exemplary embodiment as described above—to bring about the initiation of the delivery stroke on the transport and entraining rail. Whereas FIG. 22 illustrates a perspective view predominantly from below, FIG. 23 shows a longitudinal section. It is possible that the tongue 13 is glued to the pusher rod 19, welded to it or crimped with it. In the end, two very precise stops are made available, allowing a very accurate working with the medical shaft-type instrument 1.

The retaining rail 12 does not only have a retaining function for the clamps 8, namely the prevention of the return motion of the clamps 8 during the return stroke into the neutral position of the transport and entraining rail 16, but (as seen in cross-section) also defines the lower limitation of the clip line formed by the clamps 8. Further, the retaining lugs 35 should be realized in the manner of barbs which can be run over in one direction by the clamps 8 and can also be displaced by the latter.

The retaining rail 12 is also supposed to be fixed on the tube wall of the outer tube 5 by means of retaining rail mounting lugs 46 which can be seen in FIGS. 24 to 27. To this end, a mounting hole 47 is provided in the outer tube 5. The mounting hole 47 is worked into the material in the form of a slit for instance by means of a laser cutting procedure. An outer tube fold area 48, provided in the manner of a lug and comprising an inspection window 49, is bent radially inwards and offers sufficient space so that the retaining rail mounting lug 46 can engage below a lower edge 50 limited by the outer tube fold area 48.

This results in an axial stop toward the proximal end, provided with the reference symbol 51, and an axial stop toward distal, provided with the reference symbol 52. A height fixation means 53 is realized by the lower edge 50.

The mounting hole 47 is shaped in the manner of a window. The inspection window 49 is for checking purposes during the assembly process. In this way, a self-catching system is realized. The outer tube fold area 48, which acts as a lug and is formed in one piece on the outer tube 5, catches the retaining rail mounting lug 46 which is a single constituent part of the retaining rail 12 formed as a metal retaining plate and fixes the metal retaining plate at a predetermined level and in an axial position.

The sequence during the assembly process is apparent from the FIGS. 25 to 27 which show the assembly protrusions of the retaining rail 12 from proximal to distal, caught under/caught by the outer tube fold area 48 with the retaining rail mounting lug 46. FIG. 24 shows the completely assembled state.

A modified exemplary embodiment is shown in FIG. 28 in which the retaining rail 12 is fixed on the spring support 42 by means of cut-outs. The spring support 42 for its part is already immobilized on the outer tube 5 in radial and axial direction. In this arrangement, the spring support 42 comprises cams 54, which penetrate the retaining rail 12 and fix both components to each other in a form- and/or force-fitting manner. Here too, a cam 40 enters an elongated hole 39, so that a limitation of the delivery stroke is reached if the cam 40 hits the stop edge 43, which is advantageous with a force-controlled use of the handle. In fact, the handle switches over the direction of movement as from a specific limit value on. An active retraction of the transport and entraining rail 16 and of the tongue 13 is then possible.

FIGS. 29 to 31 have their focus on a distal end of the retaining rail 12. At this place, a bridge/abutment plate 55 is formed which facilitates the gliding of the clamp 8 into the shell forms 28 of the upper jaw part branch 9 and the lower jaw part branch 10. The bridge/abutment plate 55 may also be referred to as a cover for the lower jaw part 10. In addition, a retaining rail mounting hole 56 is provided, which is arranged between the bridge/abutment plate 55 and a kicker- or ski jump-like deflector 57. This deflector 57 serves in the manner of a kicker for lifting the clamp 8 at its tail, i.e. at its proximal end, so that the clamp 8 slides better into the upper and lower jaw part branch 9 and 10, respectively. The deflector 57 also serves for stiffening purposes. During the assembly process, the retaining rail mounting hole 56 is used by an assembly tool (not shown), in order to be hooked in place there.

In FIG. 32, laterally protruding retaining rail mounting lugs 46 offset in longitudinal direction are connected to each other by a (theoretical) asymmetrical bending line 58, so that the (theoretical) direct bending line 59 provided with the reference symbol 59 does not occur. Such a direct bending line 59 orthogonal relative to the longitudinal direction is avoided, as asymmetrical bending lines 58 are preferred in the event of the occurrence of critical torsional forces, because torsional forces do not occur here.

Spring lugs 60 which serve for supporting the retaining rail 12 on the pusher tube 21 can be seen in FIG. 33. Thus, a residual force is made available which tries to decrease the clip channel into which the clamps 8 are directed. This results in a mutual stabilization of all components and prevents the clamps 8 from missing the retaining lugs 32 upon retraction. Otherwise, retaining lugs 32 having a larger height and requiring more power would then be necessary, which would result in higher friction, entailing an increased physical effort during the feed motion process. In the end, a compensation of tolerances is also achieved by the spring lugs. As an alternative or in addition, the spring lugs 60 could rest on the upper and/or lower jaw part branch 9 and 10, respectively.

FIGS. 34 to 43 have their focus on the tongue 13 and its special configuration. The tongue 13 has its distal end provided with a tissue-protecting protrusion 61 which prevents that any tissue of the organ to be treated enters the area between the clamp webs/legs 29 of the clamp 8 and is pinched here unintentionally. The tissue-protecting protrusion 61 may also be referred to as a tissue spacer 61. At a site proximal relative thereto, a notch 62 is provided which forms an insertion opening 63. The insertion recess may be synonymously referred to as insertion opening 63.

As can be seen particularly clear in FIGS. 40 and 41, this insertion opening 63 allows the proximal portion of the clamp 8, namely the clamp web/leg 29, to swivel or enter into the free zone provided by the notch 62. The insertion opening 63 may also be referred to as an insertion recess and makes it possible that a portion of the clamp 8 projects from below into the notch 62 at least by some extent or even right through it.

Further, a protrusion in the manner of a movement-guiding element 64 is formed on the underside of the tongue 13. This movement-guiding element 64 is formed in the manner of a deflector 65 or pilot bead 66. It has the effect of increasing the flexural rigidity and at the same time provides for a catching protection. The catching protection prevents the clamp 8 from undesirably contacting the tongue 12 in the area of impact edges 67, as otherwise the clamp 8 would be moved in axial direction ahead of time or in the wrong sense. Abutment edges 68 for providing a targeted pushing effect on the clamp 8 are provided as well. This abutment edge 68 may also be referred to as a pushing edge or thrust lug. This is why it is provided with the reference symbol 69. The tongue rests against a part of a clamp web 29 over the length designated with the reference line 70. In this context, the insertion opening 63 also enables that the contact between the tongue 13 and the clamp 8 is maintained during the tilting of the clamp 8.

The tissue-protecting protrusion 61 with its protective function for animal or human tissue can be clearly deduced from FIG. 34. The guiding effect of the movement-guiding element 64/deflector 65/pilot bead 66 can be clearly taken from FIGS. 35 to 39 and 43. Here, it can also be clearly seen that the pilot bead 66 prevents the clamp 8 from getting caught. The movement-guiding element 64 also enhances the stiffness of the tongue 13. In this way, a catching protection and an edge shielding function are provided in addition to an anti-bulging function. This is why the clamp 8 cannot get caught on a folded sheet metal portion of the tongue 13. This may also be referred to as "edge shielding".

The tongue 13 is threaded through several clamps 8 without taking the function of guiding it. It is an elongated element with a high proneness of kinking in the course of advancing and guiding the most distal clip/the most distal clamp 8, with smallest tolerances. A lengthwise flange 71 prevents the tongue 13 from buckling. Longitudinal beads as shown in FIGS. 34 to 43 also have an anti-buckling effect. The point of the tongue 13 allows to reliably grasp the clamp 8, and the transmission of forces onto the clamp 8 in the event of an angular or positional change is achieved just as the compensation of tolerances. Implementing the tip as a flexible portion, for instance by using a material with smaller thickness, by the provision of elasticity holes, by means of cut-outs for reducing the bending forces, allows to achieve an advantageous embodiment. All those special lug or tip shapes are advantageous which prevent the thrust lugs 69 from getting levered out. The situation of the tongue 13 slipping off from a clamp web/leg 29 is effectively prevented in the manner described above.

The tissue-protecting protrusion 61 protrudes beyond the sheet metal at the tip of the tongue and is in abutment on the inner side of a clamp 8 in the leg fillet provided there. It is to be noted that the deflector 65/the pilot bead 66 has the same depth as the flange 71 of the tongue 13, to prevent any thrust transmission to the clamp 8.

In the following FIGS. 44 to 51, the spring support 42 is illustrated and explained in more detail. The spring support 42 comprises a holding catch/a cam 72 provided for being hooked into the retaining rail 12 in order to establish an axial and/or radial fixation. Further, the spring support 42 comprises a cam/a lug 73 for immobilizing the spring support on the outer tube 8.

Said cam 73 is surrounded by a sealing surface 74. The latter serves for sealing off the recess in the outer tube 5, so that no fluid can escape from the shaft-type instrument towards outside, and fluids from outside the shaft-type instrument 1 should not reach its interior either. The area which forms the sealing surface 74 is designed in the manner of a dome spring which is provided with the reference symbol 75. Thus, the wedge-shaped cam 73 lies within the sealing surface 74 of the dome spring 75. This dome spring 75 gets caulked radially in one direction, because it is arranged so as to be off-center.

The holding catch 72 and a recess accommodating it may be designed such that the respective fixations of the metal retaining plate 12 on the spring support 42 in radial and axial direction are effected separate from each other. In this case, the tolerances can be better used as if this was performed on a component in both directions. This is why a protrusion 76 is provided which is only designed for axially supporting the retaining rail 12, whereas the holding catches 72 are designed for the radial fixation. Thus, the spring support 42 has shell design having a positive effect on the elasticity. The spring support 42 serves for the fixation on the outer tube 5. It may be implemented as an injection-molded part comprising a central feed-through for guiding the pusher rod/feed rod 19. It may be designed in the manner of an integrated annular spring and comprise a springy, thin-walled oversize bulge. An extensive contact around the cam 73, being configured in the manner of a retaining cam, is advantageous in terms of producing tightness. A protrusion/retaining cam having a centering effect engages in the outer tube 5 easier if it has chamfered edges. Such chamfered edges may be provided on all protrusions or lugs. The spring support 42 is firmly clipped in place on the retaining rail 12. Thus, the spring support 42 comprises a through-hole 77 provided in the longitudinal direction and having the function of guiding the feed rod 19.

FIG. 50 shows the state of the spring support 42 in the state when clipped in place in the metal retaining plate forming the retaining rail 12. This situation is also illustrated in FIG. 51.

The bridge/abutment plate 55 may also be referred to as an abutment plate. Further, the retaining rail mounting hole 56 may be briefly referred to as a mounting hole.

The invention claimed is:

1. A medical shaft-type instrument comprising:
an instrument head for applying clamps, the instrument head being connectable via an instrument shaft to an instrument handle for actuating the instrument head; and
a clip magazine having a housing, in which magazine a plurality of clamps are bunkered at a predetermined storage position spacing relative to each other according to a storage principle,
all the clamps being movable forward, each by one storage position by a reciprocatable transport and entraining rail within the scope of a single delivery stroke, the transport and entraining rail having one clamp entraining element per clamp,
wherein adjacent clamp entraining elements are spaced from one another by first distances, and adjacent clamps are spaced from one another by second distances, the first distances being different from the second distances such that entrainment of the clamps is carried out within the scope of one single delivery stroke in a clocked way.

2. The medical shaft-type instrument according to claim 1, wherein said transport and entraining rail and the clamps are adapted to one another such that the clamps are deposited between two delivery strokes in the shaft-type instrument in other distances than predefined by the transport and entraining rail.

3. The medical shaft-type instrument according to claim 1, wherein the clamp entraining elements, storage positions predetermined by retaining lugs of a retaining rail, the clamps, and the transport and entraining rail moving the clamps during movement in a distal direction are adapted to one another such that:
initially, a proximal clamp is moved, and subsequently during a delivery stroke, distally downstream clamps are moved, or
initially, a distal clamp is moved, and subsequently proximally upstream clamps are moved.

4. The medical shaft-type instrument according to claim 3, wherein distances between the retaining lugs are different.

5. The medical shaft-type instrument according to claim 3, wherein each retaining lug, when run over by the clamps during their way to the distal end of the instrument head, is bound on the retaining rail in a bendable or swiveling way out of the motion path of the clamps to a sufficient extent, wherein during the retraction of the transport and entraining rail the retaining lugs get out of the way.

6. The medical shaft-type instrument according to claim 5, wherein each retaining lug, in a manner of a butterfly lug, is bound in a bendable or swiveling way about a bending or swivel axis which is aligned transverse to a longitudinal direction of the retaining rail.

7. The medical shaft-type instrument according to claim 6, wherein two wings of a butterfly lug form each retaining lug, with each of the wings being bendable or swiveling about a bending or swivel line crossing one another distally or proximally relative to the retaining lug.

8. The medical shaft-type instrument according to claim 3, wherein the retaining lugs have a geometry and a material that are configured such that said retaining lugs lie down substantially flat when run over by the clamps.

9. The medical shaft-type instrument according to claim 3, wherein the retaining rail as a retaining plate is made from a metallic material.

10. The medical shaft-type instrument according to claim 1, wherein the first distances between the clamp entraining elements are different.

11. The medical shaft-type instrument according to claim 1, further comprising a retaining rail in the clip magazine for storing the clamps,
wherein one of said clamps which is closest to the instrument head is transportable by a tongue into the instrument head for being ejected and bent, and
wherein the retaining rail, the transport and entraining rail, and the tongue are arranged in a stacked construction in an area of the clip magazine.

12. The medical shaft-type instrument according to claim 11, wherein the retaining rail, the transport and entraining rail and the tongue are arranged stacked upon each other in a direction which is transverse to a direction defined by a longitudinal axis of the shaft-type instrument.

13. The medical shaft-type instrument according to claim 11, wherein the tongue is arranged between the retaining rail and the transport and entraining rail.

14. The medical shaft-type instrument according to claim 11, wherein a jaw part is formed at a distal end of the instrument head, into which distal end the most distal clamp is transferable by the tongue for the interaction with an element, a vessel or an organ to be treated.

15. The medical shaft-type instrument according to claim 1, wherein:
the instrument head comprises a jaw part and is intended for applying said clamps, the jaw part connectable to the instrument handle for actuating the instrument head via the instrument shaft, the instrument shaft comprising an outer tube; and
the clip magazine comprises a retaining rail fixed in the clip magazine, the retaining rail for storing said clamps at said predetermined storage position spacing relative to each other according to said storage principle,
the medical shaft-type instrument further comprising retaining lugs spaced from each other, the clamp entraining elements being provided on the retaining rail and on the transport and entraining rail, said retaining lugs and clamp entraining elements, when the clamps slide over said retaining lugs and clamp entraining elements, are designed so as to swivel away out of a clamp slipway in the respectively other direction in an elastic fashion,
a number of said retaining lugs and/or clamp entraining elements is/are formed in a butterfly shape comprising two stop wings capable of being tilted relative to each other in a transport direction, and/or
a number of said retaining lugs and/or clamp entraining elements is/are formed so as to have a supporting wedge shape comprising a tip which is pivotable transverse to the transport direction and is provided at a distal free edge.

16. The medical shaft-type instrument according to claim 15, wherein a stop plate or stop face is formed on the retaining lugs and/or clamp entraining elements so as to extend essentially perpendicular or at least oblique to the transport direction.

17. The medical shaft-type instrument according to claim 15, wherein the tongue is supported by the transport and entraining rail and/or the retaining rail.

18. The medical shaft-type instrument according to claim 17, further comprising spring lugs projecting from the retaining rail toward the tongue in a supportive manner.

19. A medical shaft-type instrument comprising:
an instrument head for applying clamps, the instrument head being connectable via an instrument shaft to an instrument handle for actuating the instrument head; and
a clip magazine having a housing, in which magazine a plurality of clamps are bunkered at a predetermined storage position spacing relative to each other according to a storage principle,
all the clamps being movable forward, each by one storage position by a reciprocatable transport and entraining rail within the scope of a single delivery stroke, the transport and entraining rail having one clamp entraining element per clamp,
wherein adjacent clamp entraining elements are spaced from one another by first distances, and adjacent clamps are spaced from one another by second distances, the first distances being different from the second distances such that entrainment of the clamps is carried out within the scope of one single delivery stroke in a clocked way,
wherein the first distances between the clamp entraining elements are different,
wherein the medical shaft-type instrument further comprises a retaining rail with retaining lugs,
wherein the first distances between the clamp entraining elements correspond to distances between the retaining lugs, or a relative change in the first distances between the clamp entraining elements is smaller or larger than a relative change in distances between the retaining lugs.

20. The medical shaft-type instrument according to claim 19, further comprising form-fitting elements representing a part of the transport and entraining rail or of the retaining rail, wherein an average spacing alteration of the form-fitting elements contacting the clamps in relation to average spacing amounts to approximately 0.1% to 4%.

21. A medical shaft-type instrument comprising:
an instrument head for applying clamps, the instrument head being connectable via an instrument shaft to an instrument handle for actuating the instrument head; and
a clip magazine having a housing, in which magazine a plurality of clamps are bunkered at a predetermined storage position spacing relative to each other according to a storage principle,
all the clamps being movable forward, each by one storage position by a reciprocatable transport and entraining rail within the scope of a single delivery stroke, the transport and entraining rail having one clamp entraining element per clamp,
wherein adjacent clamp entraining elements are spaced from one another by first distances, and adjacent clamps are spaced from one another by second distances, the first distances being different from the second distances such that entrainment of the clamps is carried out within the scope of one single delivery stroke in a clocked way,
wherein the clamp entraining elements, storage positions predetermined by retaining lugs of a retaining rail, the clamps, and the transport and entraining rail moving the clamps during movement in a distal direction are adapted to one another such that:
initially, a proximal clamp is moved, and subsequently during a delivery stroke, distally downstream clamps are moved, or
initially, a distal clamp is moved, and subsequently proximally upstream clamps are moved, and
wherein a height of at least some of the retaining lugs measured transverse to an axial direction is so large that it guides a tongue, which is guided through the clamps for ejecting the most distal clamp and/or that it prevents a buckling of the tongue.

22. A medical shaft-type instrument comprising:
an instrument head having a jaw part and intended for applying clamps, the instrument head being connected to an instrument handle for actuating the jaw part via an instrument shaft comprising an outer tube; and
a clip magazine in which a retaining rail for storing a number of clamps at a predetermined storage position spacing relative to each other according to a storage principle is fixed,
all the clamps being movable forward, each by one storage position by a reciprocatable transport and entraining rail within a scope of a single delivery stroke,
one of said clamps which is closest to the instrument head being transportable by a tongue into the jaw part, the tongue being bound on the transport and entraining rail via a coupling device in such a manner that the transport and entraining rail is entrained in the event of a triggered feed motion for a delivery stroke upon reaching or exceeding a specific feed travel, wherein the coupling device uses a cam/elongated hole combination for a delayed transmission of forces and movements from a feed rod to the transport and entraining rail.

23. The medical shaft-type instrument according to claim 22, wherein the coupling device is formed as a feed divider as a component which is:

separate from the tongue and the transport and entraining rail; or is formed as a component which is realized in one piece with the tongue or the transport and entraining rail.

24. The medical shaft-type instrument according to claim 22, wherein a tongue-side cam engages an elongated hole on the transport and entraining rail side for establishing a form lock.

* * * * *